US008615287B2

(12) United States Patent
Harlev et al.

(10) Patent No.: US 8,615,287 B2
(45) Date of Patent: Dec. 24, 2013

(54) CATHETER TRACKING AND ENDOCARDIUM REPRESENTATION GENERATION

(75) Inventors: Doron Harlev, Cambridge, MA (US); Adam Pidlisecky, Salem, MA (US)

(73) Assignee: Rhythmia Medical, Inc., Burlington, MA (US)

( * ) Notice: Subject to any disclaimer, the term of this patent is extended or adjusted under 35 U.S.C. 154(b) by 0 days.

(21) Appl. No.: 12/871,336

(22) Filed: Aug. 30, 2010

(65) Prior Publication Data

US 2010/0324414 A1 Dec. 23, 2010

Related U.S. Application Data

(63) Continuation of application No. 11/672,562, filed on Feb. 8, 2007.

(51) Int. Cl.
*A61B 5/05* (2006.01)

(52) U.S. Cl.
USPC ........... 600/424; 600/425; 600/431; 600/433; 600/506; 600/509; 600/547

(58) Field of Classification Search
USPC .......... 600/424, 425, 431, 433, 506, 509, 547
See application file for complete search history.

(56) References Cited

U.S. PATENT DOCUMENTS

| | | | |
|---|---|---|---|
| 4,649,924 A | 3/1987 | Taccardi | |
| 4,674,518 A | 6/1987 | Salo | |
| 4,840,182 A | 6/1989 | Carlson | |
| 4,920,490 A | 4/1990 | Isaacson | |
| 5,156,151 A | 10/1992 | Imran | |
| 5,284,142 A | 2/1994 | Goble et al. | |
| 5,297,549 A | 3/1994 | Beatty et al. | |
| 5,300,068 A | 4/1994 | Rosar et al. | 606/34 |
| 5,341,807 A | 8/1994 | Nardella | |
| 5,381,333 A | 1/1995 | Isaacson et al. | |
| 5,469,858 A | 11/1995 | Osborne | |
| 5,480,422 A | 1/1996 | Ben-Haim | |
| 5,500,011 A | 3/1996 | Desai | |
| 5,553,611 A | 9/1996 | Budd et al. | |
| 5,568,809 A | 10/1996 | Ben-Haim | |

(Continued)

OTHER PUBLICATIONS

Adams, Rolf et al., "Seeded Region Growing", *IEEE transactions on pattern analysis and machine intelligence*, [0162-8828] Adams yr: 1994, vol. 16, iss. 6, p. 641, (1994).

(Continued)

*Primary Examiner* — Unsu Jung
*Assistant Examiner* — Joseph M Santos Rodriguez
(74) *Attorney, Agent, or Firm* — Fish & Richardson P.C.

(57) ABSTRACT

Methods and systems are disclosed for determining information about a position of an object within a distribution of materials having different complex conductivities. The method includes: (i) causing current to flow in the distribution; (ii) measuring an electrical signal at each of multiple locations in the distribution of materials in response to the current flow; (iii) providing spatial information about the distribution of materials with respect to a first reference frame, the spatial information indicative of regions of different complex conductivity in the distribution of materials; and (iv) determining the position of the object with respect to the spatial information about the distribution of materials based on measured electrical signals and the spatial information. In certain embodiments, the object is a catheter inserted into a patients heart cavity for cardiac mapping.

13 Claims, 13 Drawing Sheets

(56) References Cited

U.S. PATENT DOCUMENTS

| | | | |
|---|---|---|---|
| 5,577,502 A | 11/1996 | Darrow et al. | |
| 5,588,429 A | 12/1996 | Isaacson et al. | |
| 5,634,469 A | 6/1997 | Bruder et al. | |
| 5,662,108 A | 9/1997 | Budd et al. | |
| 5,687,737 A | 11/1997 | Branham et al. | |
| 5,697,377 A | 12/1997 | Wittkampf | |
| 5,704,365 A | 1/1998 | Albrecht et al. | |
| 5,722,402 A | 3/1998 | Swanson et al. | |
| 5,840,025 A | 11/1998 | Ben-Haim | |
| 5,840,031 A | 11/1998 | Crowley | |
| 5,846,198 A | 12/1998 | Killmann | 600/424 |
| 5,848,972 A | 12/1998 | Triedman et al. | |
| 5,921,982 A | 7/1999 | Lesh et al. | |
| 5,954,665 A | 9/1999 | Ben-Haim | |
| 5,971,933 A | 10/1999 | Gopakumaran et al. | |
| 5,983,126 A * | 11/1999 | Wittkampf | 600/509 |
| 6,050,267 A | 4/2000 | Nardella et al. | |
| 6,095,150 A | 8/2000 | Panescu et al. | 128/899 |
| 6,167,296 A | 12/2000 | Shahidi | |
| 6,226,542 B1 | 5/2001 | Reisfeld | |
| 6,236,886 B1 | 5/2001 | Cherepenin et al. | |
| 6,240,307 B1 | 5/2001 | Beatty et al. | |
| 6,246,898 B1 | 6/2001 | Vesely et al. | |
| 6,254,536 B1 | 7/2001 | DeVito | 600/300 |
| 6,278,894 B1 | 8/2001 | Salo et al. | 600/547 |
| 6,298,257 B1 | 10/2001 | Hall et al. | 600/407 |
| 6,308,093 B1 | 10/2001 | Armoundas et al. | 600/509 |
| 6,314,310 B1 | 11/2001 | Ben-Haim et al. | |
| 6,317,619 B1 | 11/2001 | Boernert et al. | 600/410 |
| 6,318,375 B1 | 11/2001 | Plicchi et al. | |
| 6,360,123 B1 | 3/2002 | Kimichi et al. | 600/547 |
| 6,368,285 B1 | 4/2002 | Osadchy et al. | |
| 6,400,981 B1 | 6/2002 | Govari | |
| 6,516,807 B1 | 2/2003 | Panescu et al. | |
| 6,547,082 B1 | 4/2003 | Babini | |
| 6,556,695 B1 | 4/2003 | Packer et al. | |
| 6,574,492 B1 | 6/2003 | Ben-Haim et al. | |
| 6,574,498 B1 | 6/2003 | Gilboa | 600/424 |
| 6,593,884 B1 | 7/2003 | Gilboa et al. | |
| 6,600,948 B2 | 7/2003 | Ben-Haim et al. | |
| 6,603,996 B1 | 8/2003 | Beatty et al. | |
| 6,631,290 B1 * | 10/2003 | Guck et al. | 600/509 |
| 6,640,119 B1 | 10/2003 | Budd et al. | |
| 6,650,927 B1 | 11/2003 | Keidar | |
| 6,690,963 B2 | 2/2004 | Ben-Haim et al. | |
| 6,701,176 B1 | 3/2004 | Halperin et al. | |
| 6,728,562 B1 | 4/2004 | Budd et al. | |
| 6,773,402 B2 | 8/2004 | Govari et al. | |
| 6,807,439 B2 | 10/2004 | Edwards et al. | 600/420 |
| 6,839,588 B1 | 1/2005 | Rudy | |
| 6,847,839 B2 | 1/2005 | Ciaccio et al. | |
| 6,872,428 B2 | 3/2005 | Yang et al. | |
| 6,892,090 B2 | 5/2005 | Verard et al. | 600/424 |
| 6,892,091 B1 * | 5/2005 | Ben-Haim et al. | 600/509 |
| 6,939,309 B1 | 9/2005 | Beatty et al. | |
| 6,957,101 B2 | 10/2005 | Porath et al. | |
| 6,978,168 B2 | 12/2005 | Beatty et al. | |
| 6,990,370 B1 * | 1/2006 | Beatty et al. | 600/509 |
| 7,016,719 B2 | 3/2006 | Rudy et al. | |
| 7,043,292 B2 | 5/2006 | Tarjan et al. | |
| 7,263,397 B2 | 8/2007 | Hauck et al. | 600/374 |
| 7,505,810 B2 | 3/2009 | Harlev et al. | |
| 7,515,954 B2 | 4/2009 | Harlev et al. | |
| 7,729,752 B2 | 6/2010 | Harlev et al. | |
| 2002/0151807 A1 | 10/2002 | Goldin | |
| 2003/0018251 A1 | 1/2003 | Solomon | |
| 2003/0065271 A1 | 4/2003 | Khoury | |
| 2003/0076277 A1 | 4/2003 | Muramatsu et al. | |
| 2003/0078509 A1 | 4/2003 | Panescu | |
| 2003/0216630 A1 * | 11/2003 | Jersey-Willuhn et al. | 600/407 |
| 2004/0077942 A1 | 4/2004 | Hall et al. | |
| 2004/0097806 A1 | 5/2004 | Hunter et al. | |
| 2004/0243015 A1 | 12/2004 | Smith et al. | |
| 2004/0254437 A1 | 12/2004 | Hauck et al. | |
| 2005/0038337 A1 | 2/2005 | Edwards | 600/424 |
| 2005/0054918 A1 | 3/2005 | Sra | |
| 2005/0107834 A1 | 5/2005 | Freeman et al. | |
| 2005/0154282 A1 | 7/2005 | Li et al. | |
| 2005/0288599 A1 | 12/2005 | MacAdam et al. | |
| 2006/0085049 A1 | 4/2006 | Cory et al. | |
| 2006/0116575 A1 | 6/2006 | Willis | |
| 2006/0122526 A1 | 6/2006 | Berenfeld et al. | |
| 2006/0173251 A1 | 8/2006 | Govari et al. | 600/306 |
| 2006/0178587 A1 | 8/2006 | Khoury | |
| 2006/0241401 A1 | 10/2006 | Govari et al. | |
| 2007/0016007 A1 | 1/2007 | Govari et al. | |
| 2007/0038078 A1 | 2/2007 | Osadchy | 600/424 |
| 2007/0049821 A1 | 3/2007 | Willis | |
| 2007/0197929 A1 | 8/2007 | Porath et al. | |
| 2007/0265539 A1 | 11/2007 | Hastings et al. | |
| 2007/0287902 A1 * | 12/2007 | Fuimaono et al. | 600/410 |
| 2007/0299351 A1 | 12/2007 | Harlev et al. | 600/509 |
| 2007/0299352 A1 | 12/2007 | Harlev et al. | |
| 2008/0190438 A1 | 8/2008 | Harlev et al. | |
| 2008/0221566 A1 | 9/2008 | Krishnan | |
| 2008/0234588 A1 | 9/2008 | Feldman et al. | |
| 2008/0249424 A1 | 10/2008 | Harlev et al. | |
| 2009/0171274 A1 | 7/2009 | Harlev et al. | |
| 2009/0177072 A1 | 7/2009 | Harlev et al. | |
| 2009/0253976 A1 | 10/2009 | Harlev et al. | |
| 2010/0286551 A1 | 11/2010 | Harlev et al. | |

OTHER PUBLICATIONS

Ben-Haim, Shlomo A. et al., "Nonfluoroscopic, In Vivo Navigation and Mapping Technology", Nat. Med. 2: pp. 1393-1395, (1996).

Besl, Paul J. et al., "A Method For Registration of 3-D Shapes", *IEEE transactions on pattern analysis and machine intelligence*, vol. 14 No. 2, (Feb. 1992).

Blomström-Lundqvist, Carina et al., "Acc/Aha/Esc Guidelines For the Ma Nagement of Patientswith Supraventricular Arrhythmias", *J Am Coll Cardiol*.;vol. 42, No. 8, pp. 1493-1531 (Oct. 15, 2003).

Brooks, Dana et al., "Electrical Imaging of the Heart", *Signal Processing Magazine*, IEEE, vol. 14, Issue: 1 (Jan. 1997).

De Groot, Natasja M.S. et al., "Three-Dimensional Catheter Positioning During Radiofrequency Ablation In Patients", *J Cardiovasc Electrophysiol*, vol. 11, pp. 1183-1192, (Nov. 2000).

Dong, Jun et al., "Integrated Electroanatomic Mapping With Three-Dimensional Computed Tomographic Images For Real-Time Guided Ablations", *Circulation*,; 113(2): pp. 186-194, (Jan. 17, 2006).

Durrer, Dirk et al., "Total Excitation of the Isolated Human Heart", *Circulation*, vol. XLI, (Jun. 1970).

Ector, Joris et al., "Cardiac Three-Dimensional Magnetic Resonance Imaging and Fluoroscopy Merging", *Circulation*, (Dec. 13, 2005).

Firedman, Paul, "Novel Mapping Techniques For Cardiac Electrophysiology", Heart;87:pp. 575-582 (2002).

Geddes, L.A. et al., "Criteria for the Selection of Materials for Implanted Electrodes", *Annals of Biomedical Engineering*, vol. 31, pp. 879-890 (2003).

Gepstein, Lior et al., "A Novel Method For Nonfluoroscopic Catheter-Based Electroanatomical Mapping of the Heart", *Circulation*; 95, pp. 1611-1622, (1997).

Huang, Yi-Chih et al., "Development of a Third Generation Intraventricular Impedance Imaging (Iii) System Evaluation of Hardware Design", *Engineering in Medicine and Biology Society*, Proceedings of the 19th Annual International Conference of the IEEE, Oct. 30-Nov. 2, 1997 vol. 6, (1997).

Jané, Raimon et al, "Alignment Methods For Averaging of High Resolution Cardiac Signals", *IEEE Transactions in Biomedical Engineering*, vol. 38 No. 6, (Jun. 1991).

Jia, Ping et al., "Electrophysiologic Endocardial Mapping From a Noncontact Nonexpandable Catheter", *J Cardiovasc Electrophysiol*, vol. 11, pp. 1238-1251, (Nov. 2000).

Kistler, Peter M. et al., "Validation of Three-Dimensional Cardiac Image Integration", *J Cardiovasc Electrophysiol*, vol. 17, pp. 341-348, (Apr. 2006).

Kun, Stevan et al., "Conductance Volumetric Model of an Eccentrically Positioned Catheter Within a Three-Compartment Ellipsoidal Ventricle", U, IEEE Transactions on, Jun. 1993, vol. 40, Issue: 6.

(56) References Cited

OTHER PUBLICATIONS

Laciar, Eric et al., "Improved Alignment Method For Noisy High-Resolution Ecg and Holter Records Using Multiscale Cross-Correlation", *IEEE Transactions on Biomedical Engineering*, vol. 50, No. 3, (Mar. 2003).

Makela, Timo et al., "A Review of Cardiac Image Registration Methods", *IEEE Transactions on Medical Imaging*, vol. 21, No. 9, (Sep. 2002).

Malladi, R. et al., "A Geometric Approach to Segmentation and Analysis of 3D Medical Images", *Mathematical Methods in Biomedical Image Analysis*, Proceedings of the Workshop on, Jun. 21-22, 1996, pp. 244-252, (1996).

Mangan, Alan et al., "Partioning 3D Surface Meshes Using Watershed Segmentation", *IEEE Transactions on Visualization and Computer Graphics*, vol. 05, No. 4, pp. 308-321, (Oct.-Dec. 1999).

Merrill, Daniel R. et al., "Electrical stimulation of excitable tissue: design of efficacious and safe protocols", *Journal of Neuroscience Methods*, vol. 141, pp. 171-198 (2005).

Noseworthy, Peter A. et al., "The Impact of Respiration on Left Atrial and Pulmonary Venous Anatomy: Implications For Image-Guided Intervention", *Heart Rhythm*, vol. 2, No. 11, (Nov. 2005).

Pappone, Carlo et al., "Robotic Magnetic Navigation For Atrial Fibrillation Ablation", *Journal of the American College of Cardiology*, vol. 47, No. 7, (2006).

Paragios, Nikos, "A Level Set Approach For Shape-Driven Segmentation and Tracking of the Left Ventricle", *IEEE Transactions on Medical Imaging*, vol. 22, No. 6, (Jun. 2003).

Persson, Per-Olof et al., "A Simple Mesh Generator in Matlab", *SIAM Review*, vol. 46 (2), pp. 329-345, (Jun. 1, 2004).

Pham, Dzung et al., "Current Methods In Medical Image Segmentation", *Annu. Rev. Biomed. Eng.*, 02: pp. 315-337, (2000).

Rao, Liyun et al., "Novel Noncontact Catheter System For Endocardial Electrical And Anatomical Imaging", *Annals of Biomedical Engineering*, vol. 32, No. 4, pp. 573-584, (Apr. 2004).

Reddy, Vivek et al., "Integration of Cardiac Magnetic Resonance Imaging With Three-Dimensional Electroanatomic Mapping to Guide Left Ventricular Catheter Manipulation", *Journal of the American College of Cardiology*, vol. 44, No. 11, (2004).

Solomon, Stephen B. et al., "Real-Time Cardiac Catheter Navigation on Three-Dimensional Ct Images", *Journal of Interventional Cardiac Electrophysiology*, 8, pp. 27-36, (2003).

Sra, Jasbir et al, "Registration of 3D Computed Tomographic Images With Interventional Systems: Implications For Catheter Ablation of Atrial Fibrillation", *J Interv Card Electrophysiol*, 16: pp. 141-148, (2006).

Sra, Jasbir et al. "Registration of Three-Dimensional Left Atrial Computed Tomographic Images With Projection Images Obtained Using Fluoroscopy", *Circulation*, (Dec. 13, 2005(.

Stevenson, William J. et al., "Radiofrequency Catheter Ablation of Ventricular Tachycardia After Myocardial Infarction", Circulation. ;98, pp. 308-314. (1998).

Thal, Sergio G. et al., "Novel Applications In Catheter Ablation", *Journal of Interventional Cardiac Electrophysiology*, 13, pp. 17-21, (2005).

Wittkampf, Fred H. et al., "Localisa : New Technique For Real-Time 3-Dimensional Localization of Regular Intracardiac Electrodes", *Circulation*, 99: pp. 1312-1317, (1999).

Yezzi, Anthony et al., "A Geometric Snake Model For Segmentation", *IEEE Transactions on Medical Imaging*, vol. 16, No. 2, (Apr. 1997).

Notification of Transmittal of the International Search Report and the Written Opinion of the International Searching Authority, or the Declaration, 11 pages, Aug. 8, 2008.

Notification of Transmittal of the International Search Report and the Written Opinion of the International Searching Authority, or the Declaration, PCT/US2009/036099, Dated Apr. 28, 2009, 21 pages.

Arthur, "Clinical Use of Intracardiac Impedance: Current Applications and Future Perspectives", PACE, vol. 24:500-506, Apr. 2001.

Authorized officer Gunter Held, Supplementary European Search Report in European Application No. 08728501.1, mailed Feb. 25, 2011, 4 pages.

Authorized officer Nora Lindner, International Preliminary on Patentability in PCT/US2008/052385, mailed Aug. 20, 2009, 7 pages.

Baan, Jan et al., "Continuous Measurement of Left Ventricular Volume in Animals and Humans By Conductance Catheter", Circulation, vol. 70,pp. 812-823, (1984).

Badies, "Real-Time Reconstruction of Endocardial Potential Maps in Non-Contact Cardiac Mapping", International Journal for computation and Mathematics in Electrical Engineering (COMPEL), vol. 28, No. 4, 2009.

Breithardt et al., "AHA Medical/Scientific Statement—Special Report: Standards for Analysis of Ventricular Late Potentials Using High-Resolution or Signal-Averaged Electrocardiography", *Circulation*, 83(4):1481-1488, 1991.

Caspi et al., "Stem Cell Research: Regenerating the Heart Using Human Embryonic Stem Cells—from Cell to Bedside", *IMAJ*, 8:208-214, 2006.

Cheney et al., "Electrical Impedance Tomography", SIAM Review 41:85-101, 1999.

Donahue et al., "Focal Modification of Electrical Conduction in the Heart by Viral Gene Transfer", *Nature Medicine*, 6(12):1395-1398, 2000.

E. J. Haug, K. K. Choi, V. Komkov: Design Sensitivity Analysis of Structural Systems, Mathematics in Science and Engineering, vol. 177 (1986).

Friedman, "Catheter Cryoablation of Cardiac Arrhythmias", *Current Opinion in Cardiology*, 20:48-54, 2005.

Jain et al., "Cell Therapy Attenuates Deleterious Ventricular Remodeling and Improves Cardiac Performance After Myocardial Infarction", *Circulation*, 103:1920-1927, 2001.

Jalife, "Rotors and Spiral Waves in Atrial Fibrillation", *Journal of Cardiovascular Electrophysiology*, 14:776-780, 2003.

Kikuchi et al., "Targeted Modification of Atrial Electophysiology by Homogeneous Transmural Atrial Gene Transfer", *Circulation*, 111:264-270, 2005.

Kuklik et al., "The reconstruction, from a set of points, and analysis of the interior surface of the heart chamber", Physiol. Meas. 25:617-627, 2004.

L. Piegl, W. Tiller: The NURBS Book, 2nd Edition, Springer (1997).

Liu et al., "Endocardial Potential Mapping From a Noncontact Nonexpandable Catheter: A Feasibility Study", *Annals of Biomedical Engineering*, 26:994-1009, 1998.

Lorensen et al. "Marching Cubes: A High Resolution 3D Surface Construction Algorithm". Computer Graphics 21(4):163-169, Jul. 1987.

Meininger et al., "Initial Experience with a Novel Focused Ultrasound Ablation System for Ring Ablation Outside the Pulmonary Vein", *Journal of Interventional Cardiac Electrophysiology*, 8:141-148, 2003.

Miller, "Editor's Forum—Application of Registration for Ablation: A Marriage of Technologies", *Journal of Interventional Cardiac Electrophysiology*, 11:87-89, 2004.

Nademanee et al., "A New Approach for Catheter Ablation of Atrial Fibrillation: Mapping of the Electrophysiologic Substrate", *Journal of the American College of Cardiology*, 43(11):2044-2053, 2004.

Persson, "Mesh Generation for Implicit Geometries", *Massachusetts Institute of Technology—Thesis*, Feb. 5, 2006.

Reddy et al., "Use of a Diode Laser Balloon Ablation Catheter to Generate Circumferential Pulmonary Venous Lesions in an Open-Thoracotomy Caprine Model", *PACE*, 27:52-57, 2004.

Sanders et al., "Spectral Analysis Identifies Sites of High-Frequency Activity Maintaining Atrial Fibrillation in Humans", *Circulation*, 112:789-797, 2005.

Sethian. "Level Set Methods and Fast Marching Methods: Evolving Interfaces in Computational Geometry, Fluid Mechanics, Computer Vision, and Materials Science". *Department of Mathematics-University of California, Berkeley*. Cambridge University Press, 1999.

(56) References Cited

OTHER PUBLICATIONS

Simon et al., "Electroanatomic Mapping of the Right Atrium With a Right Atrial Basket Catheter and Three-Dimensional Intracardiac Echocardiography", *PACE*, 27:318-326, 2004.

Smits et al., "Catheter-Based Intramyocarial Injection of Autologous Skeletal Myoblasts as a Primary Treatment of Ischemic Heart Failure", *Journal of the American College of Cardiology*, 42(12):2063-2069, 2003.

Taccardi et al., "A New Intracavitary Probe for Detecting the Site of the Origin of Ectopic Ventricular Beats During One Cardiac Cycle", *Circulation*, 75(1):272-281, 1987.

Thiagalingam et al., "Noncontact Mapping of the Left Ventricle: Insights from Validation With Transmural Contact Mapping", *PACE*, 27:570-578, 2004.

Voth, "The Inverse Problem of Electrocardiography: Industrial Solutions and Simulations", BEM and NFSI Conference Proceedings, Minneapolis, MN, May 12-15, 2005, pp. 191-194.

\* cited by examiner

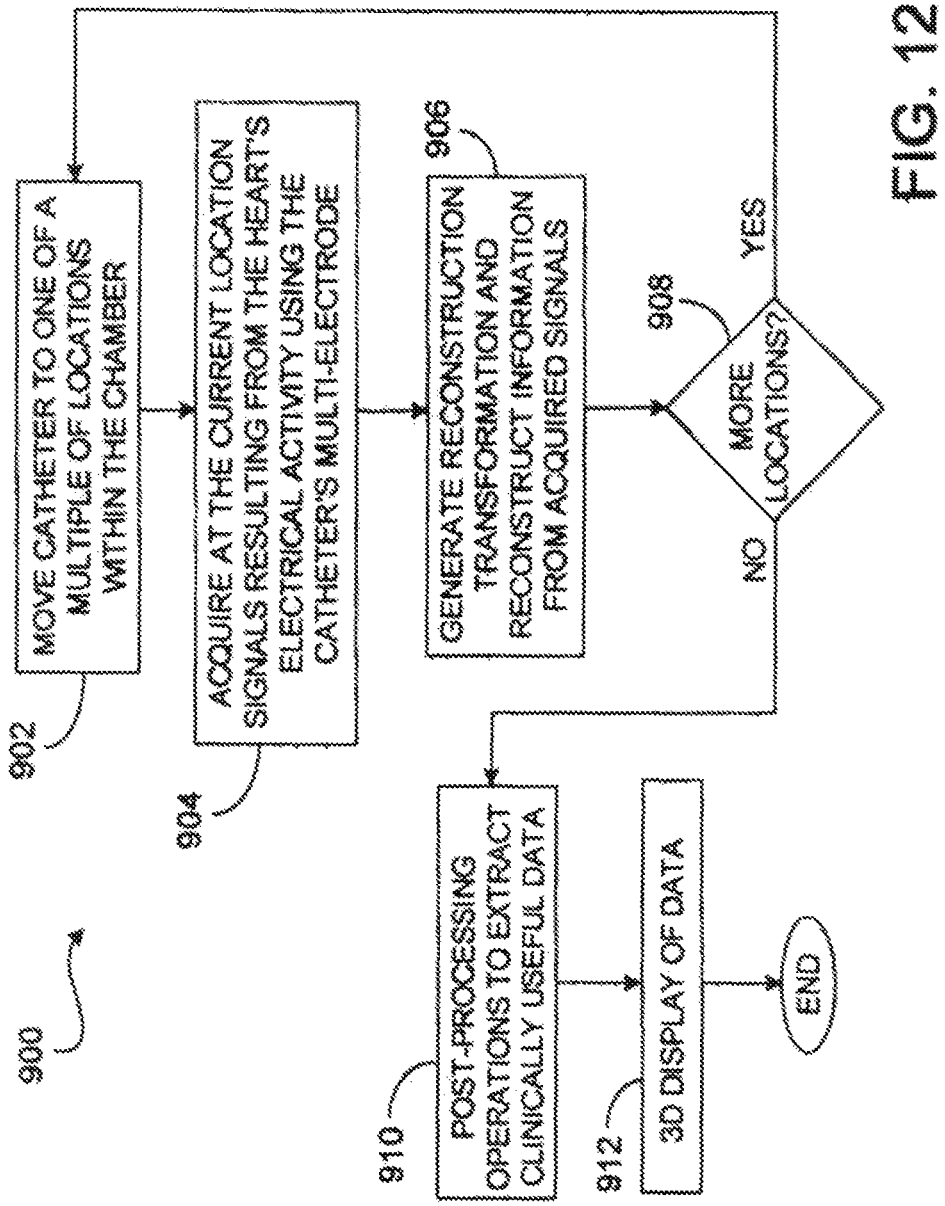

CATHETER TRACKING AND ENDOCARDIUM REPRESENTATION GENERATION

CROSS REFERENCE TO RELATED APPLICATIONS

Pursuant to 35 USC §120, this application is a continuation and claims the benefit of U.S. application Ser. No. 11/672,562, filed Feb. 8, 2007. The application (U.S. application Ser. No. 11/672,562) is incorporated herein by reference in its entirety.

TECHNICAL FIELD

This invention relates to determining the position of an object, such as tracking the position of a catheter in a patient's heart cavity, and to the registration of a representation of a space, such as a 3D representation of the patient's heart cavity, to a coordinate system used to track the catheter.

BACKGROUND

Use of minimally invasive procedures, such as catheter ablation, to treat a variety of heart conditions, such as supraventricular and ventricular arrhythmias, is becoming increasingly more prevalent. Such procedures involve the mapping of electrical activity in the heart, such as at various locations on the endocardium surface ("cardiac mapping"), to identify the site of origin of the arrhythmia followed by a targeted ablation of the site. To perform such cardiac mapping a catheter with one or more electrodes can be inserted into the patient's heart chamber.

Under some circumstances, the location of the catheter in the heart chamber is determined using a tracking system. One type of a tracking system that may be used to track the location of the catheter inside the heart chamber is an independent tracking system based on the use of magnetic or electric fields to sense and track the location of the catheter. The location of a catheter tracked using such an independent tracking system is thus provided in terms of the tracking system's coordinates system.

The matching of the catheter's location according to the independent tracking system and a coordinate system corresponding to some type of 3D anatomical representation of the heart cavity, is called coordinate system registration.

SUMMARY

In general, in one aspect, a method is disclosed for determining information about a position of an object within a distribution of materials having different complex conductivities. The method includes: (i) causing current to flow in the distribution; (ii) measuring an electrical signal at each of multiple locations in the distribution of materials in response to the current flow; (iii) providing spatial information about the distribution of materials with respect to a first reference frame, the spatial information indicative of regions of different complex conductivity in the distribution of materials; and (iv) determining the position of the object with respect to the spatial information about the distribution of materials based on measured electrical signals and the spatial information.

Embodiments of the method may include any of the following features.

The regions of different complex conductivity can include regions of having different real parts of the complex conductivity, regions having different imaginary parts of the complex conductivity, or regions having different real parts and different imaginary parts of the complex conductivity. Similarly, the measured electrical signals can include information about the amplitude, phase, or both.

The spatial information can be indicative of a position dependent complex conductivity throughout the distribution of materials, the position dependent complex conductivity including a conductivity value for each of the different materials in the distribution.

Causing the current to flow in the distribution can include causing the current to flow between each of multiple pairs of electrodes. The electrical signals can then be measured for each pair of electrodes that cause the current to flow. At least some of the electrodes that cause current to flow can be located on different regions of the object. At least some of the electrical signals can be measured by corresponding electrodes on the object.

Determining the position of the object with respect to the spatial information about the distribution of materials can include determining coordinates for the position of the object in the first reference frame. The method can further include repeating the causing, measuring, and determining steps to track the position of the object in the first reference frame as it moves through the distribution of materials.

Determining the position of the object with respect to the spatial information can include tracking movement of the object in a second reference frame and determining a transformation for registering the first reference frame with the second reference frame.

Determining the position of the object relative to the first reference frame can include determining a location of a point of the object in the first reference frame and an orientation of the object in the first reference frame.

Determining the position of the object relative to the first reference frame can include using an optimization algorithm that minimizes differences between the measured electrical signals and predicted signals determined from the spatial information about the distribution of materials as a function of the relative position. Moreover, the optimization algorithm can further determine a conductivity value for each of one or more of the materials in the distribution of materials.

In certain embodiments, the distribution of materials includes a patient's heart cavity and the object is a catheter inserted into the patient's heart.

The spatial information about the distribution of materials can be based on one or more of: a computed tomography (CT) image; a magnetic resonance imaging (MRI) image; a fluoroscopic rotational angiography image; and an ultrasound image.

At least some of the electrodes that cause the current to flow can be located on different regions of the catheter. Alternatively, or in addition, at least some of the electrodes that cause the current to flow can be located on a second catheter positioned in the patient's heart cavity.

The catheter can include spatially distributed electrodes to measure at least some of the electrical signals produced in response to the injected current. The electrodes on the catheter can be further used to measure electrical signals indicative of cardiac electrical activity. For example, the current can be injected at frequencies spaced from those corresponding to the cardiac electrical activity. The method can further include frequency processing the measured electrical signal to distinguish electrical signals indicative of cardiac electrical activity from those responsive to the injected current.

The information about electrical activity in the heart cavity can be based on the measured electrical signals, the spatial information about the heart cavity, and the determined relative position of the catheter. The method can further include displaying the information about the electrical activity in the heart on a representation of the patient's heart. The method can further include treating a patient's heart condition based on the displayed information about the electrical activity in the heart.

The catheter can include current injection electrodes for injecting current into the patient's heart cavity that are different from the electrodes used measure electrical signals. The surface area of each current injection electrode can be larger than the surface area of each electrode used to measure an electrical signal. The surface of each current injection electrode can have a coating to reduce its electrical impedance with respect to blood in the heart cavity. More generally, every electrode on the catheter can include such a coating.

The catheter can include multiple pairs of current injection electrodes. For example, the current injection electrodes can be positioned at opposite ends of a deployed configuration for the catheter with respect to each of multiple axes. The catheter can be deployable in a rigid configuration. Furthermore, the catheter can be configured for non-contact deployment in each of multiple locations within the heart.

The method can further include repeating the causing, measuring, and determining steps to track the position of the catheter in the heart with respect to the first reference frame.

The catheter can further include at least one tracking element whose position in a second reference frame is detectable by an independent tracking system. For example, the method can further include using the determined information about the position of the catheter to register the first and second reference frames. Registering the first and second reference frame can include determining a transformation that maps the locations of measuring electrodes in the first reference frame to the locations of measuring electrodes in the second reference frame.

The method further includes repeating the causing and measuring steps as the catheter is moved to each of multiple locations within the heart, wherein the position of the object is determined based on the measured electrical signals for all of the multiple catheter locations, the spatial information about the distribution of materials, and relative changes in the position of the catheter corresponding to the multiple locations.

The spatial information corresponds to an average of the geometrical configuration of the heart cavity over multiple cardiac cycles. Alternatively, the spatial information can corresponds to a specific point in a cardiac cycle. The method can further include synchronizing the injecting and the measuring with respect to the cardiac cycle.

In general, in another aspect, a method is disclosed for determining a transformation for registering first and second reference frames for a distribution of materials. The method includes: (i) causing current to flow in the distribution; (ii) measuring an electrical signal at each of multiple locations in the distribution of materials to in response to the current flow; (iii) providing spatial information about the distribution of materials with respect to the first reference frame, the spatial information indicative of regions of different complex conductivity in the distribution of materials; (iv) providing positions in the second reference frame for the multiple locations at which the electrical signals are measured; and (v) determining the transformation based on the measured electrical signals, the spatial information about the distribution of materials, and the positions in the second reference frame for the multiple locations at which the electrical signals are measured. For example, the distribution of materials may include a patient's heart cavity, wherein at least some of the electrical signals are measured by electrodes on a catheter inserted into the heart cavity, and wherein the second reference frame corresponds to coordinates provided by a tracking system for the catheter.

Embodiments of the method may include any features described above in connection with the first method.

In general, in another aspect, a system is disclosed for determining information about a position of an object within a distribution of materials having different complex conductivities The system includes: (i) electronics for causing current to flow in the distribution; (ii) electronics for measuring an electrical signal at each of multiple locations in the distribution of materials in response to the current flow; and (iii) an electronic processor coupled to current causing and signal measuring electronics, wherein the electronic processor is configured to determine the position of the object with respect to spatial information about the distribution of materials based on the measured electrical signals and the spatial information, wherein the spatial information is indicative of regions of different complex conductivity in the distribution of materials with respect to a first reference frame.

Embodiments of the system may include any of the following features.

The regions of different complex conductivity can include regions of having different real parts of the complex conductivity, regions having different imaginary parts of the complex conductivity, or regions having different real parts and different imaginary parts of the complex conductivity. Similarly, the measured electrical signals can include information about the amplitude, phase, or both of the respective electrical signals.

The spatial information can be indicative of a position dependent complex conductivity throughout the distribution of materials, the position dependent complex conductivity including a conductivity value for each of the different materials in the distribution.

The object can include electrodes coupled to the measuring electronics for measuring the electrical signals.

The object can include electrodes that cause at least some of the current to flow. For example, the object can include multiple pairs of current injecting electrodes coupled to the current causing electronics for causing the current to flow between each pair of the current injecting electrodes. The object can also include measuring electrodes positioned on the object and coupled to the measuring electronics to measure the electrical signals in response to current flow between each pair of current injecting electrodes.

The determination of the position of the object relative to the first reference frame by the electronic processor includes determining a location of a point of a point of the object in the first reference frame and an orientation of the object in the first reference frame.

The determination of the position of the object with respect to the spatial information about the distribution of materials by the electronic processor can include determining coordinates for the position of the object in the first reference frame.

The electronic processor can be configured to track the position of the object in the first reference frame as it moves through the distribution of materials in response to additional current flow and electrical signal measurements by the electronics.

The determination of the position of the object with respect to the spatial information by the electronic processor can include tracking movement of the object in a second reference frame and determining a transformation for registering the first reference frame with the second reference frame.

The determination of the position of the object relative to the first reference frame by the electronic processor can include using an optimization algorithm that minimizes differences between the measured electrical signals and predicted signals determined from the spatial information about the distribution of materials as a function of the relative position. The optimization algorithm can further determine a conductivity value for each of one or more of the materials in the distribution of materials.

In certain embodiments, the distribution of materials includes a patient's heart cavity, and the object is a catheter configured to be inserted into the patient's heart, and wherein the system includes the catheter.

The spatial information about the distribution of materials can be based on one or more of: a computed tomography (CT) image; a magnetic resonance imaging (MRI) image; a fluoroscopic rotational angiography image; and an ultrasound image.

The catheter can include current injecting electrodes coupled to the current causing electronics for causing the current to flow. The system can further include a second catheter including additional current injecting electrodes coupled to the current causing electronics. The catheter can include spatially distributed electrodes coupled to the measuring electronics to measure at least some of the electrical signals produced in response to the injected current. The current injection electrodes on the catheter for injecting current into the patient's heart cavity can be the same or different from the electrodes used measure the electrical signals.

The surface area of each current injection electrode can be larger than the surface area of each electrode used to measure an electrical signal.

The surface of each current injection electrode can have a coating to reduce its electrical impedance with respect to blood in the heart cavity. More generally, all of the catheter electrodes can include such a coating.

The catheter can include multiple pairs of current injection electrodes. For example, the current injection electrodes can be positioned at opposite ends of a deployed configuration for the catheter with respect to each of multiple axes.

The catheter can be configured for non-contact deployment in each of multiple locations within the heart.

The electronic processor can be further configured to use electrical signals measured by the electrodes on the catheter to determine information about cardiac electrical activity. For example, the current causing electronics can cause the current to be injected at frequencies spaced from those corresponding to the cardiac electrical activity. The measuring electronics can then be configured to frequency process the measured electrical signal to distinguish electrical signals indicative of cardiac electrical activity from those responsive to the injected current.

The information about cardiac electrical activity can be based on the measured electrical signals, the spatial information about the heart cavity, and the determined relative position of the catheter. The electronic processor can be further configured to display the information about the electrical activity in the heart on a representation of the patient's heart. The system can further include an ablation catheter for treating a patient's heart condition based on the displayed information about the cardiac electrical activity.

The electronic processor can be configured to track the position of the catheter in the heart with respect to the first reference frame in response to the current injection and signal measuring.

The system can further include at least one tracking element coupled to the catheter and an independent tracking system coupled to the electronic processor for providing the position of the tracking element in a second reference frame. For example, the electronic processor can further be configured to use the determined information about the position of the catheter to register the first and second reference frames. Registering the first and second reference frames can include determining a transformation that maps the locations of the measuring electrodes in the first reference frame to the locations of the measuring electrodes in the second reference frame.

The electronic processor can be configured to process the measured signals for each of multiple catheter locations within the heart, wherein the position of the catheter is determined based on the measured electrical signals for all of the multiple catheter locations, the spatial information about the distribution of materials, and relative changes in the position of the catheter corresponding to the multiple locations.

The spatial information can correspond to an average of the geometrical configuration of the heart cavity over multiple cardiac cycles. Alternatively, the spatial information can correspond to a specific point in a cardiac cycle. For example, the electronics can be configured to synchronize the current injection and the signal measuring with respect to the cardiac cycle.

In general, in another aspect, a system is disclosed for determining a transformation for registering first and second reference frames for a distribution of materials. The system includes: (i) electronics for causing current to flow in the distribution; (ii) electronics for measuring an electrical signal at each of multiple locations in the distribution of materials in response to the current flow; and (iii) an electronic processor coupled to the current causing and signal measuring electronics and configured to determine the transformation based on the measured electrical signals, a spatial information about the distribution of materials with respect to the first reference frame, and positions in the second reference frame for the multiple locations at which the electrical signals are measured. The spatial information about the distribution of materials with respect to the first reference frame is indicative of regions of different complex conductivity in the distribution of materials. In certain embodiments, the distribution of materials includes a patient's heart cavity, wherein the system further includes a catheter configured for insertion into the heart cavity and an independent tracking system for the catheter, wherein at least some of the electrical signals are measured by electrodes on the catheter and wherein the second reference frame corresponds to coordinates provided by the tracking system for the catheter.

Embodiments of the system may further include any of the features described above in connection with the first system.

As used herein, the "position" of an object means information about one or more of the 6 degrees of freedom that completely define the location and orientation of a three-dimensional object in a three-dimensional coordinate system. For example, the position of the object can include: three independent values indicative of the coordinates of a point of the object in a Cartesian coordinate system and three independent values indicative of the angles for the orientation of the object about each of the Cartesian axes; or any subset of such values.

As used herein, "heart cavity" means the heart and surrounding tissue.

Unless otherwise defined, all technical and scientific terms used herein have the same meaning as commonly understood by one of ordinary skill in the art to which this invention belongs. In case of conflict with documents incorporated herein by reference, the present document controls.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 12 is a flow diagram of an exemplary embodiment for cardiac mapping using a multi-electrode catheter.

Like reference symbols in the various drawings indicate like elements.

DETAILED DESCRIPTION

Overview

Figure 1:
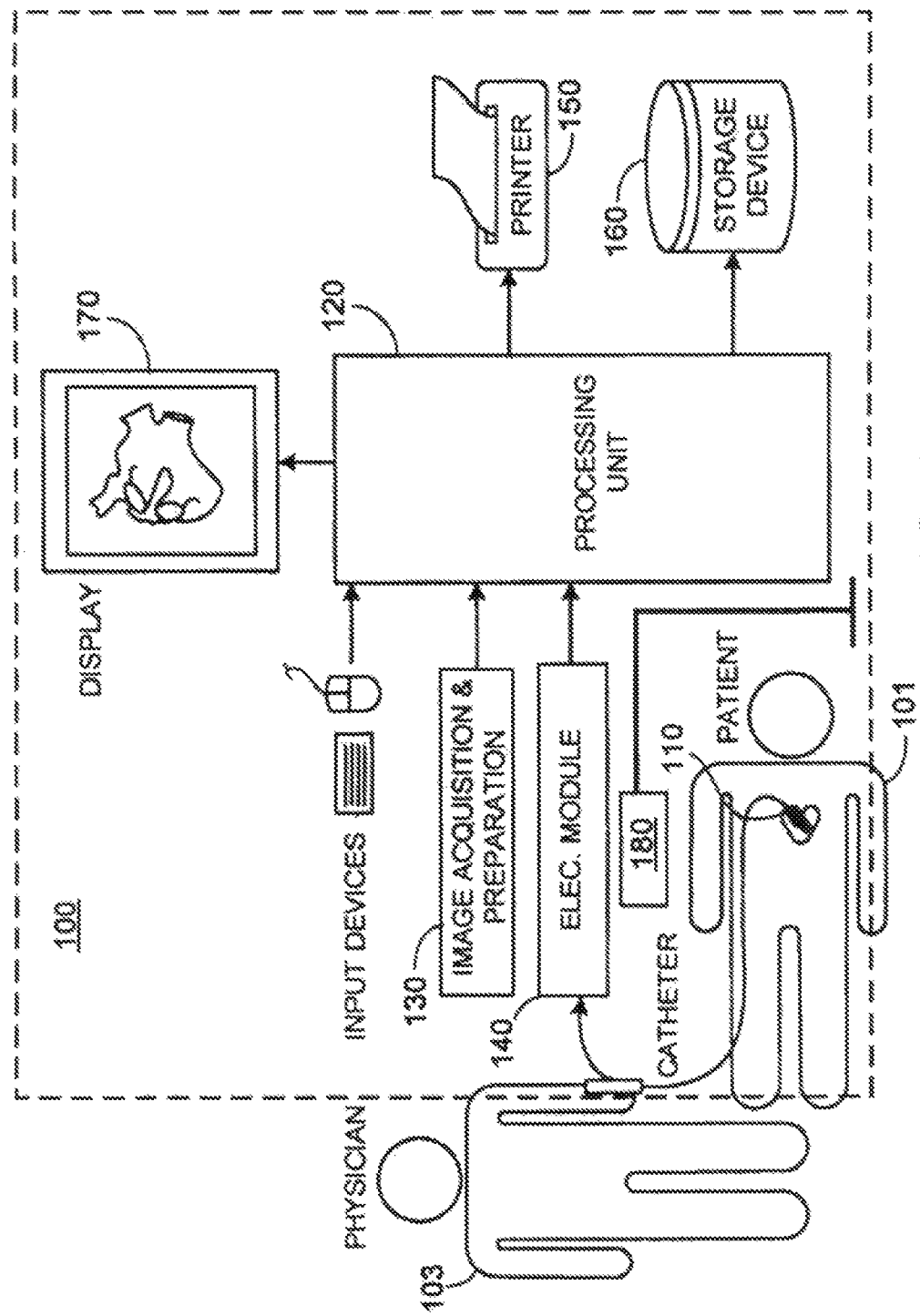
FIG. 1 is a schematic diagram of an exemplary automatic registration system.

Embodiments disclosed herein include a method and system for determining the position of a catheter in a patient's heart cavity. For example, the catheter may be configured with multiple electrodes and used for cardiac mapping, such as described in commonly owned patent application Ser. No. 11/451,898, entitled "NON-CONTACT CARDIAC MAPPING, INCLUDING MOVING CATHETER AND MULTI-BEAT INTEGRATION" and filed Jun. 13, 2006, application Ser. No. 11/451,908, entitled "NON-CONTACT CARDIAC MAPPING, INCLUDING PREPROCESSING" and filed Jun. 13, 2006, and application Ser. No. 11/451,871 entitled "NON-CONTACT CARDIAC MAPPING, INCLUDING RESOLUTION MAP" and filed Jun. 13, 2006, the contents of which are incorporated herein by reference. Generally, cardiac mapping involves determining information about the electrical activity of a patients heart (e.g., at different locations of the endocardium surface) based on electrical signals measured by the multiple electrodes of the catheter. To perform such cardiac mapping, the position of the catheter (or more generally the positions of the catheter electrodes) within the heart cavity should be known.

To determine the position of the catheter in the patient's heart cavity, certain embodiments disclosed herein cause electrical current to flow within the heart cavity. The current may originate from electrodes on the catheter itself and/or from one or more other sources that may be internal or external to the heart cavity. The potential fields generated by the injected current will depend on the conductivity profile within the heart cavity. For example, blood and heart muscle have different conductivities. The potential fields are measured at multiple locations within the heart cavity. For example, electrodes on the catheter can be used to measure the potentials. The potentials measured by the electrodes on the catheter will depend on the position of the catheter within the heart cavity. Moreover, when current is injected from one or more electrodes on the catheter, the resulting potential fields will also depend on the on the position of the catheter within the heart cavity. Accordingly, measurements made by the catheter electrodes can be used to infer information about the position of the catheter in the heart cavity.

To accurately determine the position of the catheter within the heart cavity, information about the measured potentials produced in response to the injected current is combined with separately acquired spatial information about the patient's heart cavity (e.g., magnetic resonance imaging (MRI) or computed tomography (CT) image slices of the patient's heart). Such spatial information is used to determine a 3D representation of the patient's heart cavity, including its conductivity profile. Based on this separately acquired conductivity profile, the expected potentials measured for different positions of the catheter within the heart cavity can be calculated and compared to the actual measured potentials to accurately determine the position of the catheter within the heart cavity.

In some embodiments, potentials measured in response to the injected current can be used to continuously monitor the position of the catheter in the heart cavity, even as it is moved within the heart cavity. In other embodiments, an independent tracking system is used to monitor the position of the catheter in another coordinate system, and the information about the position of the catheter determined from the measured potentials in response to the injected current and the separately acquired spatial information about the patient's heart cavity is used to register the coordinate system of the independent tracking system to that of the 3D representation of the patient's heart cavity.

In the above discussion and in the details that follow, the focus is on determining the position of a catheter in a heart cavity. However, this is only an exemplary application. In other cases, the method and systems generally disclosed herein can be applied to determining the position of any object within any distribution of materials to characterized by a conductivity profile, or to register the position of that object as measured by some independent tracking system with a 3D representation of that distribution of materials.

Furthermore, while in some of the specific embodiments that follow the signals measured by the object electrodes correspond to the relative strength (i.e., amplitude) of the measured electrical signal (e.g., potential), further embodiments may also analyze the phase of the measured signal, either alone or in combination with the amplitude of the measured signal. The phase of the measured signal is indicative of spatial variations in the imaginary part of the complex conductivity (e.g., permittivity) in the distribution of materials.

Representative System

FIG. 1 shows a schematic diagram of an exemplary embodiment of an automatic registration system 100 that includes an optional tracking system 180 to facilitate the tracking and registration of a catheter 110 inside the heart cavity of a patient 101. The catheter 110 is a moveable catheter 110 having multiple spatially distributed electrodes. The catheter is used by a physician 103 to perform various medical procedures, including cardiac mapping. During performance of the automatic registration procedure, and subsequently when the catheter acquires signals that are used to perform cardiac mapping, the catheter 110 is displaced to at least one location within the heart chamber into which the catheter 110 was inserted.

In some embodiments the catheter 110 is fitted with various types of electrodes that are configured to perform various functions. For example, the catheter 110 may include at least one pair of current injection electrodes ("CIEs") configured to inject electrical current into the medium in which the catheter 110 is disposed. The catheter 110 may also include multiple potential measuring electrodes ("PMEs") configured to measure the potentials resulting from the current injected by the current injection electrodes. In certain embodiments, the potential measuring electrodes are also used for cardiac mapping.

Figure 2A:
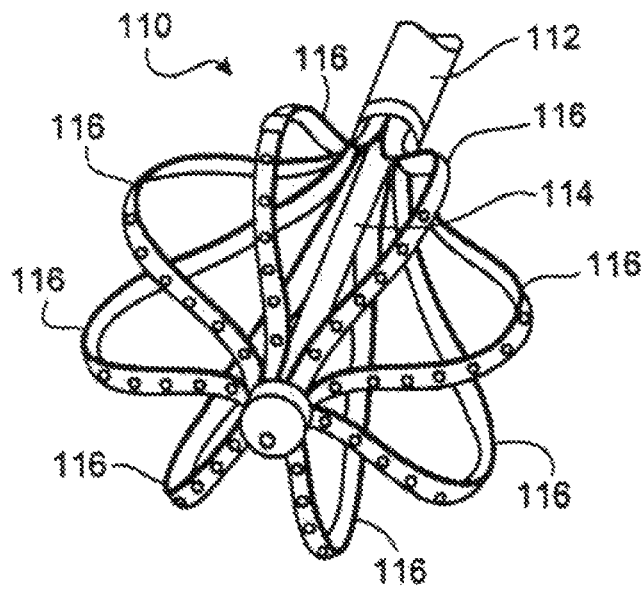
FIGS. 2a-2c show perspective, end, and side views, respectively, of a deployed catheter with multiple current injection electrodes (CIE) and multiple potential measuring electrodes (PME).
Figure 2B:
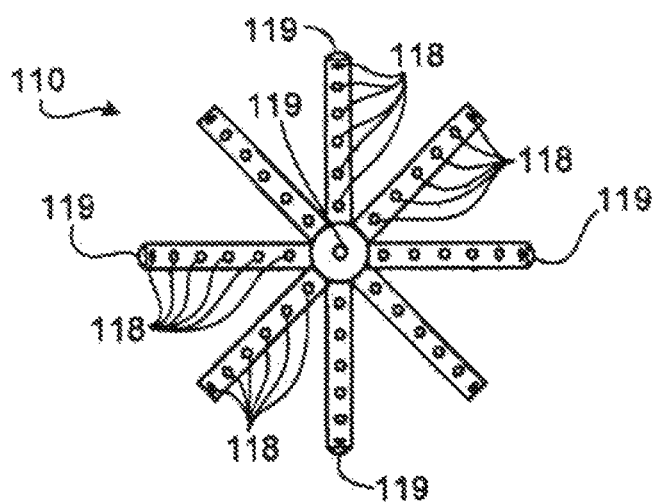
Figure 2C:
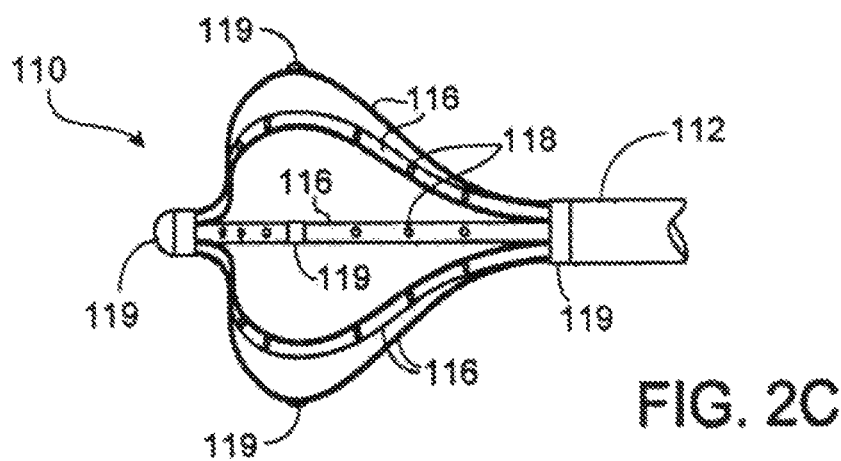

FIGS. 2a-c show different views for one embodiment of the catheter 110, which includes a base sleeve 112, a central retractable inner member 114, and multiple splines 116 connected to base sleeve 112 at one end and inner member 114 at the other end. When inner member 114 is in an extended configuration (not shown), splines 116 are pulled tight to the inner member so that catheter 110 has a narrow profile for guiding it through blood vessels. When inner member 114 is retracted (as shown in FIGS. 2a-b), splines 116 are deployed and pushed into an outward "olive" shaped configuration for use in the heart cavity. As explained in more detail below, the splines 116 each carry electrodes, so when the inner member is in the retracted configuration, the electrode are deployed in the sense that they are distributed over a greater volume.

Other known configurations may be used to deploy multi-electrode catheter 110 For example, the catheter may use a balloon, shape memory material such as Nitinol, or a polymer or other stiffening material to selectively deploy the catheter and its electrode into a desired configuration when in the patient's heart cavity. In further embodiments, the catheter geometry may be fixed, in which case it has the some configuration in the heart cavity as in the blood vessels leading to the heart cavity.

Returning to the specific catheter embodiment of FIGS. 2a-2c, FIG. 2a shows a perspective view of catheter 110, FIG. 2b shows an end-on view of catheter 110, and FIG. 2c shows a side view of catheter 110, all with the catheter in its deployed configuration. Each spline includes multiple potential measuring electrodes (PME) 118, and every other spline includes a current injection electrode (CIE) 119 at its most-outward position. Current injection electrodes (CIE) 119 are also included on sleeve 112 at the base of the splines and on the front tip of inner member 114 where the splines meet. Accordingly, in the presently described embodiment, there are three pairs of CIEs, each generally defining one axis in a Cartesian coordinate system.

The purpose of the CIEs is to inject current into the heart cavity. For example, each CIE pair can define a source and sink electrode, respectively, for injecting current into the heart cavity. More generally, however, current may be injected in the heart cavity from multiple electrodes relative to a ground electrode. The purpose of the PMEs is to measure potentials in the heart cavity in response to the current provided by the CIEs. The PMEs can also be used for cardiac mapping.

In preferred embodiments, the current injecting electrodes 119 are generally mounted at different regions of the catheter 110 so as to maximize the information collected by multiple configurations. CIE pairs that are oriented orthogonally relative to each other produce less correlated measurements, which in turn increase resolution. In addition, electrode pairs that are distant from each other also produce less correlated measurements which increase resolution. This is why in the preferred embodiment of catheter 110 shown in FIGS. 2a-2c, the CIE electrodes 119 are aligned as pairs on three orthogonal axes.

In some embodiments, like that shown in FIGS. 2a-2c, multiple CIE electrode pairs are employed so that a large sample of measured potentials in the heart cavity can be obtained to thereby improve the robustness and accuracy of the registration procedure. At some given time, any two electrodes from the CIE electrodes can be selected and activated so that one of the selected electrodes acts as the source electrode and the other electrode acts as a sink electrode. A control mechanism in electrical communication with the CIEs enables selection of any two electrodes to serve as the activated source/sink pair at a particular time. After that selected pair has been activated, and the resulting potentials in the heart cavity are measured by the multiple potential measuring electrodes, the pair of CIEs can be deactivated, and another pair of CIEs is selected to cause another electric field to be formed inside the heart cavity. Thus, the control mechanism regulates the selection and activation of the CIEs to cause a temporal sequence of injected currents to be created at different time instances, which in turn results in a temporal sequence of different electric fields formed inside the heart chamber in which the catheter 110 is deployed. The control mechanism electrically couples a signal generator to the selected electrodes. Selection of the particular electrodes to be activated can be based on a pre-determined sequence that is stored in a memory module connected to a central processor connected to the catheter 110, or it can be based on user-controlled signals that are electrically relayed to the control mechanism to cause the desired activation of the CIEs. Moreover, in further embodiments, more than a single pair of CIEs can be simultaneously activated to inject current into the heart cavity.

Referring again to FIG. 1, system 100 includes an electronics module 140 coupled to processing unit 120 for controlling the electrodes on catheter 110, including a signal generation module for injecting current into the heart cavity through the CIEs and a signal acquisition module for measuring potentials through the PMEs. The electronics module 140 can be implemented using analog or digital electronics, or a combination of both. Such exemplary configurations, which are intended to be non-limiting, are now described.

Figure 3:
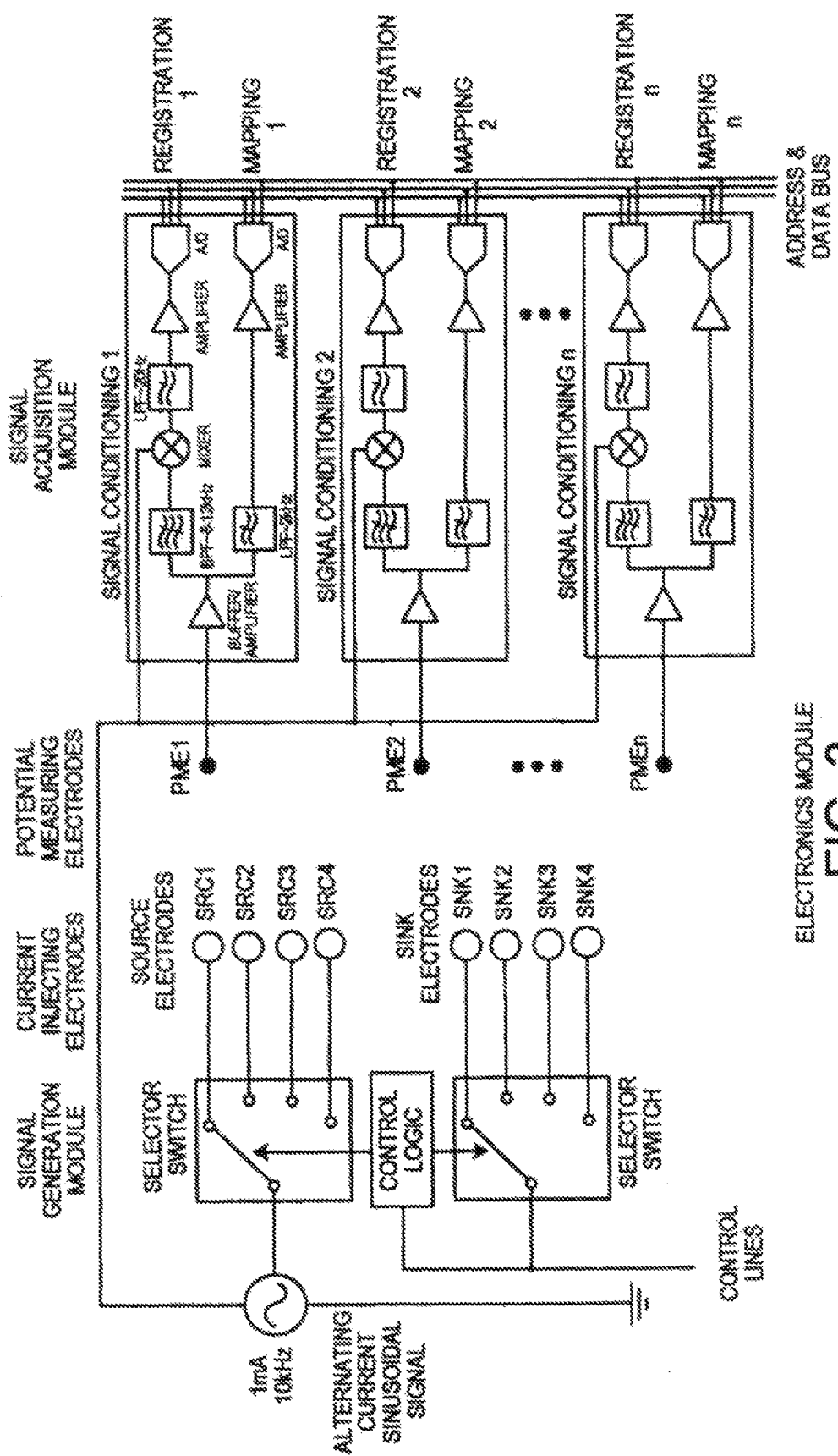
FIG. 3 is a schematic diagram of an analog implementation of a signal generation module (SGM) and signal acquisition module (SAM) for an electronics module coupled to the multi-electrode catheter.

Referring to FIG. 3, the signal generation and acquisition modules are implemented using analog hardware. The signal generation module (SGM) depicted supports 8 CIEs defining 4 source/sink electrode pairs, where SRC refers to a source electrode and SNK refers to a sink electrode. For the purpose of this example, each pair is driven using a 10 kHz oscillating 1 mA current source. A selector switch is used to select each of the pairs sequentially based on control signals provided by the processing unit or other control logic. Each channel in the signal generation module is connected to a current injecting electrode. In this case the source and sink electrodes are pre-selected permanently such that each electrode is always either a source or a sink, although this need not be the case in other embodiments The signal acquisition module (SAM) buffers and amplifies the signals as they are collected by the potential measuring electrodes. The buffer prevents the acquisition system from loading the signals collected by the electrodes. After buffering and amplification, the signals are split and filtered into two channels, one for detecting the registration signal (i.e., the signals produced in response to the CIEs) and one for detecting the signal generated by the heart's electrical activation (i.e., cardiac mapping). Because the heart's electrical activity is primarily below 2 kHz, a low pass filter (LPF) is used to separate the cardiac mapping potential signals from those produced in response to the CIEs. The low pass filter may be implemented as an active filter responsible for both filtering and amplification. The signal is then sampled by an analog to digital converter. To support bandwidth and resolution requirements the converter may sample at >4 kHz at 15 bits per sample. After sampling, the signals are passed to the processing unit for further analysis. Both the LPF and A/D may be configured such that the filter and sample frequency can be changed by software control (not drawn).

The second channel following the input buffer detects the registration signal. In this embodiment, the detection is implemented using a lock-in amplifier approach to detect amplitude. It should be appreciated that other implementation can be used to accomplish the same task. In this channel the signal is first filtered using a band pass filter (BPF) whose pass band frequency is centered on the 10 kHz generated by the SGM. Following the BPF, the signal is multiplied by the same 10 kHz signal generated by the SGM using a mixer. As a result, the signal is down converted to DC such that its value following the down conversion is proportional to its amplitude before the down-conversion. The signal is then filtered using a very narrow LPF of roughly 100 Hz. The filter bandwidth has two effects. On the one hand, the narrower the filter the better noise performance will be. On the other hand, the wider the filter, the more registration updates are available per second. A filter setting of 100 Hz provides excellent noise performance with a location update rate of roughly 20 Hz. After filtering, the signal is amplified and sampled by an analog to digital converter. The converter in this case may sample at 200 Hz using 15 bits per sample. After sampling, the signals are passed to the processing unit for further analysis. As before, the channel properties can be configured to be changed by software control (not drawn).

Figure 4:
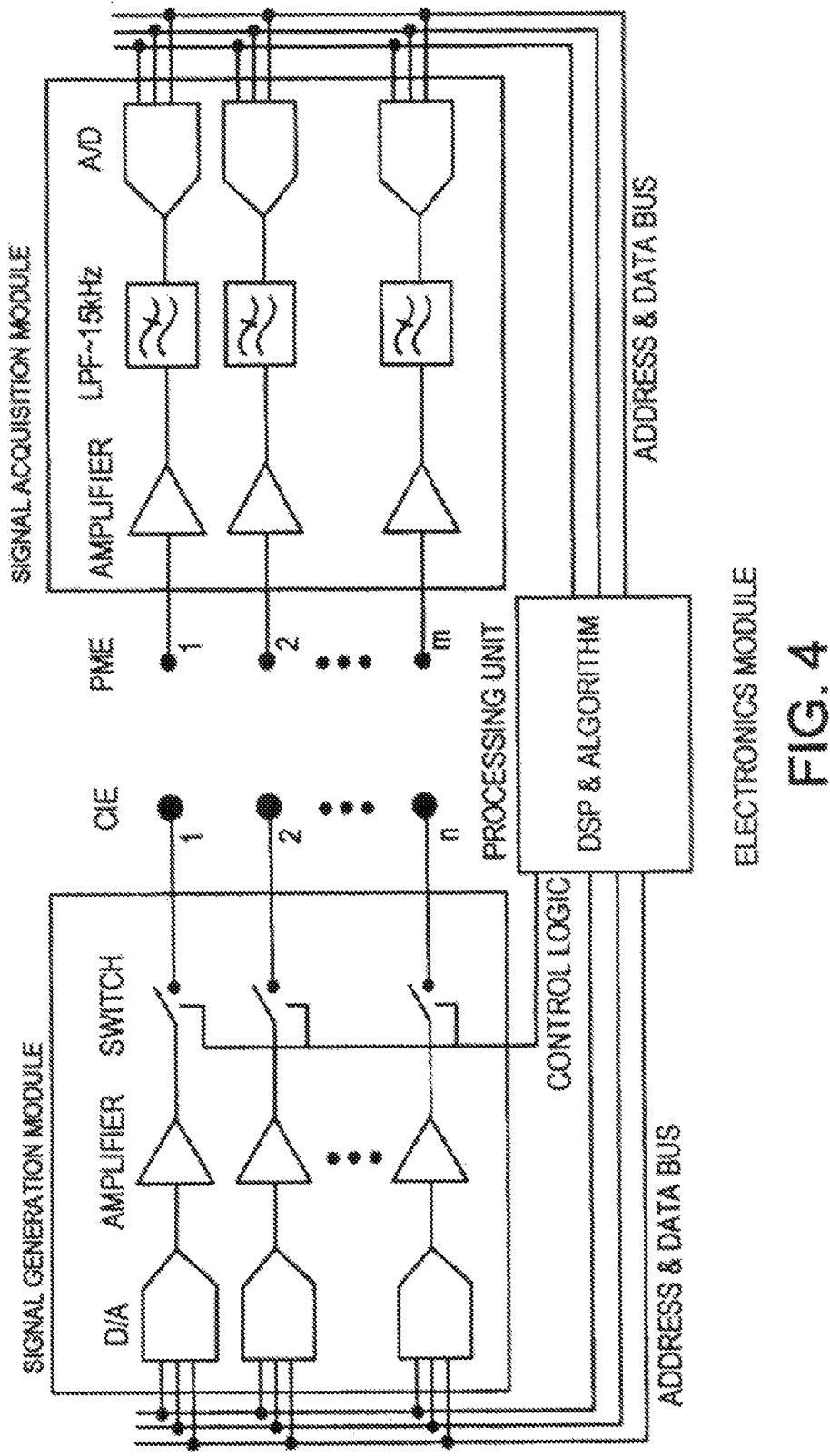
FIG. 4 is a schematic diagram of a digital implementation of a signal generation module (SGM) and signal acquisition module (SAM) for an electronics module coupled to the multi-electrode catheter.

Referring to FIG. 4, the signal generation and acquisition modules have a digital implementation. The SGM generates the required signals using an array of n digital to analog converters (D/A). In a preferred embodiment n=6. It should be appreciated that instead of n D/As it is possible to use fewer D/As and a multiplexed sample and hold amplifier. The signals generated by the D/As are controlled and timed by the processing unit. In one embodiment, the signals may mimic those described in the analog implementation whereby a sinusoidal signal is switched between electrodes. In other embodiments, however, the digital implementation provides more flexibility in that more complex signals (e.g. different frequencies, simultaneous activation of multiple electrodes) may be driven. After the conversion to an analog signal, the signals are buffered by an amplifier capable of driving the necessary current (<2 mA) at relevant frequencies (<30 kHz). After buffering, a processor controlled switch is used to support a high impedance mode. This is necessary in order to block a particular electrode from acting as a source or a sink at a particular time.

In the SAM hardware, an input stage amplifies and buffers the signal. Following amplification the signal is low pass filtered in a wide enough band such that both the heart's electrical activity (<2 kHz) and signals generated by the SGM are kept inside the filtered band. In FIG. 4 the frequency band is 15 kHz. Following the filter, the signal is sampled above Nyquist frequency (>30 kHz) at 15 bits per sample. The sampled signals are then transferred to the processing unit which uses digital signal processing (DSP) techniques to filter the two channels in each electrode and down-convert the registration signal appropriately.

A relatively small number of CIEs can result in a relatively large number of possible electrode pair combinations that can be activated to enable different potential field configurations to be formed inside the heart cavity, in which the catheter 110 is deployed and thus enhance the robustness of the registration procedure. For example, six (6) electrodes mounted on the catheter 110 can be paired into fifteen (15) combinations of different source/sink pairs, thus resulting in fifteen different potential fields, for a particular potential value, formed inside the medium. As noted above, to achieve high robustness of the registration procedure, the various source/sink electrodes disposed on the catheter 110 may be mounted at different regions of the catheter. For example, one useful configurations corresponds to that shown in FIGS. 2a-2c in which the six (6) CIEs include a pair of CIEs align along each of three orthogonal axes.

The potential measuring electrodes, configured to measure the electrical signals in the distribution of materials (e.g., the intracardiac blood) at the locations in which those electrodes are situated, are generally distributed substantially uniformly on the catheter 110. Preferably, the current injecting electrodes are designed to have low impedance at the interface between electrode and blood. The impedance between electrodes and blood is determined by the surface area of the electrode and electrode material. The larger the surface area, the lower the impedance. In one preferred embodiment, the potential measuring electrodes would have dimensions of 100 μm×100 μm, yielding a surface area of a surface area of 10,000 μm$^2$, while the current injecting electrodes would have dimensions of 1 mm×1 mm, yielding a surface area 1 mm$^2$. The larger surface area for CIEs is preferred in order to reduce their impedance at the interface to blood and allow the injection of current. The PMEs are less sensitive to blood interface impedance because they are performing the measurement with very high input impedance. Accordingly, reducing interface impedance for the PMEs is generally not as important as reducing it for the CIEs. Specialized coatings such as Platinum Black, Iridium Oxide and Titanium Nitride may also be used to reduce impedance of electrodes for a given surface area. For example, such coatings may be applied to one or more of the CIEs, one or more of the PMEs, or all of the catheter electrodes.

In some embodiments, sixty-four (64) potential measuring electrodes are used. The exact number of potential measuring electrodes that are employed depends on the dimensions of the catheter 110 and on the desired accuracy of the registration procedure.

In order to register the catheter with 6 degrees of freedom, a minimum of 6 data points are required, and thus at least six electrodes are necessary. However, given that the numerical problem is ill-conditioned, additional electrodes help better condition the problem, and consequently improve accuracy. In embodiments in which the sensing electrodes serve in the dual capacity of registration electrodes and cardiac mapping electrodes, the number of sensing electrodes to be used will also depend on the desired accuracy of the physiological information at the endocardium surface that is to be reconstructed.

As noted above, the PMEs on catheter 110 can also used for cardiac mapping, such as that described in commonly owned patent application Ser. No. 11/451,898, entitled "NON-CONTACT CARDIAC MAPPING, INCLUDING MOVING CATHETER AND MULTI-BEAT INTEGRATION" and filed Jun. 13, 2006, the contents of which are incorporated herein by reference. As also noted above, because the frequency of the current injected by CIEs (e.g., 10 kHz) is much higher than the frequency of the electrical activity of the patient's heart, the signal acquisition module can separate signals measured by the PMEs based on frequency to distinguish registration signals from cardiac mapping signals (e.g., frequencies higher than 1 kHz, and lower than 1 kHz, respectively.) Furthermore, in additional embodiments, catheter 110 may include separate electrodes used only for cardiac mapping.

As further shown in FIG. 1, the registration system 100 includes the image acquisition and preparation module 130. The acquisition and preparation module 130 receives volumetric images (e.g., CT, MRI or ultrasound images taken by a scanner apparatus) of the torso, and processes them to provide spatial information about the patient's heart cavity (or, in other non-cardiac applications, spatial information may be derived from other imaging means about some other distribution of materials.) The spatial information thus provided can subsequently be processed to include conductivity information relating to the heart chamber (or distribution of materials), to thereby provide spatial information that is indicative of position-dependent conductivity throughout the heart cavity. Thus, module 130 processes the volumetric images to provide a 3D representation of the heart cavity. The generated 3D representation of the heart cavity is then used to perform the registration operation, as will be described in greater detail below. Additionally, mapping of the data acquired by the multiple mapping electrodes of catheter 110 is subsequently performed with reference to the 3D representation of the heart cavity.

The registration system 100 further includes the processing unit 120 which performs several of the operations pertaining to the automatic registration procedure, including the determination of catheter electrode locations that result in the best fit between the measured signals and those calculated for different positions of the catheter in view of the conductivity profile corresponding to the 3D representation of the heart cavity provided by module 130. Additionally, the processing unit 120 can subsequently also perform the cardiac mapping procedure, including a reconstruction procedure to determine the physiological information at the endocardium surface from measured signals, and may also perform post-processing operations on the reconstructed physiological information to extract and display useful features of the information to the operator of the system 100 and/or other persons (e.g., a physician).

Although the position of the catheter may be determined on an ongoing basis as the catheter is moved within the heart cavity based only on the signals measured by the PMEs (and the separately acquired conductivity profile), optionally, an independent tracking system may be used track the location of the catheter 110 as it is moved inside the heart chamber. Thus, as shown in FIG. 1, the registration system 100 may include an independent tracking system 180 that provides the 3D spatial coordinates of the catheter and/or its multiple electrodes with respect to the tracking system's coordinate system. The information from the PMEs produced in response to the CIEs can be used to register the coordinate system of the tracking system to the 3D representation of the heart cavity provided by module 130.

In some embodiments, independent tracking system 180 is a conventional tracking system based on tracking electric or magnetic signals generated externally by the independent tracking system 180 and detected by one or more tracking elements, such as sensors, affixed to the catheter 110. Alternatively, tracking elements such as emitters or beacons affixed to the catheter may emit electric or magnetic signatures that are detected by the independent tracking system 180, and used to determine the location of the emitters, and thus the location and orientation of the catheter 110. For example, a collection of miniaturized coils oriented to detect orthogonal magnetic fields and forming a sensor can be placed inside the catheter to detect the generated magnetic fields. The independent tracking system 180 is generally disposed outside the patient's body at a distance that enables the system 180 to either generate radiation of suitable strength (i.e., generate signals whose amplitude will not harm the patient or otherwise interfere with the operation of other apparatus disposed in the near vicinity of the sensing and tracking system 180), or detect magnetic or electric radiation emitted by the emitters affixed to the catheter 110.

In some embodiments, the location of the electrodes relative to the catheter 110 is fixed and known, and thus the only information that needs to be determined is the location and orientation of the catheter 110 in the 3D space defined by the heart cavity. Specifically, a sensor that is affixed to the catheter 110 may be used to determine the location and orientation of the catheter. In other embodiments the location and orientation of the various electrodes relative to the catheter may vary, and accordingly, in such embodiments multiple tracking elements attached proximate to the various electrodes or the electrodes themselves in the case of impedance tracking may be used to facilitate the determination of the location of the catheter and/or its electrodes.

Alternatively and/or additionally, the independent tracking system may be based on ultrasound, impedance or fluoroscopy tracking. In impedance and fluoroscopy tracking it is possible to locate the electrode location without necessitating dedicated sensors. In the case of impedance, electrical potential generated by electric field generators are detected by the existing electrodes. In case of fluoroscopy, electrode location may be detected by an image processing scheme that identifies and tracks the electrodes and/or opaque markers located on the catheter.

The signals acquired by the various electrodes of catheter 110 during the registration procedure and/or the mapping procedure are passed to the processing unit 120 via electronics module 140. As described above, electronics module 140 can be used to amplify, filter and continuously sample intracardiac potentials measured by each electrode.

In some embodiments, the electronics module 140 is implemented by use of integrated components on a dedicated printed circuit board. In other embodiments, some of the signal conditioning tasks may be implemented on a CPU, FPGA or DSP after sampling. To accommodate safety regulations, the signal conditioning module is isolated from high voltage power supplies. The electronics module is also protected from defibrillation shock, and interference caused by nearby pacing or ablation.

The processing unit 120, image acquisition and preparation module 130 shown in FIG. 1 is a processor-based device that includes a computer and/or other types of processor-based devices suitable for multiple applications. Such devices can include volatile and non-volatile memory elements, and peripheral devices to enable input/output functionality. Such peripheral devices include, for example, a CD-ROM drive and/or floppy drive, or a network connection, for downloading related content to the connected system. Such peripheral devices may also be used for downloading software containing computer instructions to enable general operation of the respective unit/module, and for downloading software implemented programs to perform operations in the manner that will be described in more detailed below with respect to the various systems and devices shown in FIG. 1. Alternatively, the various units/modules may be implemented on a single or multi processor-based platform capable of performing the functions of these units/modules. Additionally or alternatively, one or more of the procedures performed by the processing unit 120 and/or image acquisition module 130 and/or electronics module 140 may be implemented using processing hardware such as digital signal processors (DSP), field programmable gate arrays (FPGA), mixed-signal integrated circuits, ASICS, etc. The electronics module 140 is typically implemented using analog hardware augmented with signal processing capabilities provided by DSP, CPU and FPGA devices.

As additionally shown in FIG. 1, the registration system 100 includes peripheral devices such as printer 150 and/or display device 170, both of which are interconnected to the processing unit 120. Additionally, the registration system 100 includes storage device 160 that is used to store data acquired by the various interconnected modules, including the volumetric images, raw data measured by electrodes and the resultant endocardium representation computed there from, the reconstructed physiological information corresponding to the endocardium surface, etc.

Registration Using Independent Tracking System

Figure 5:
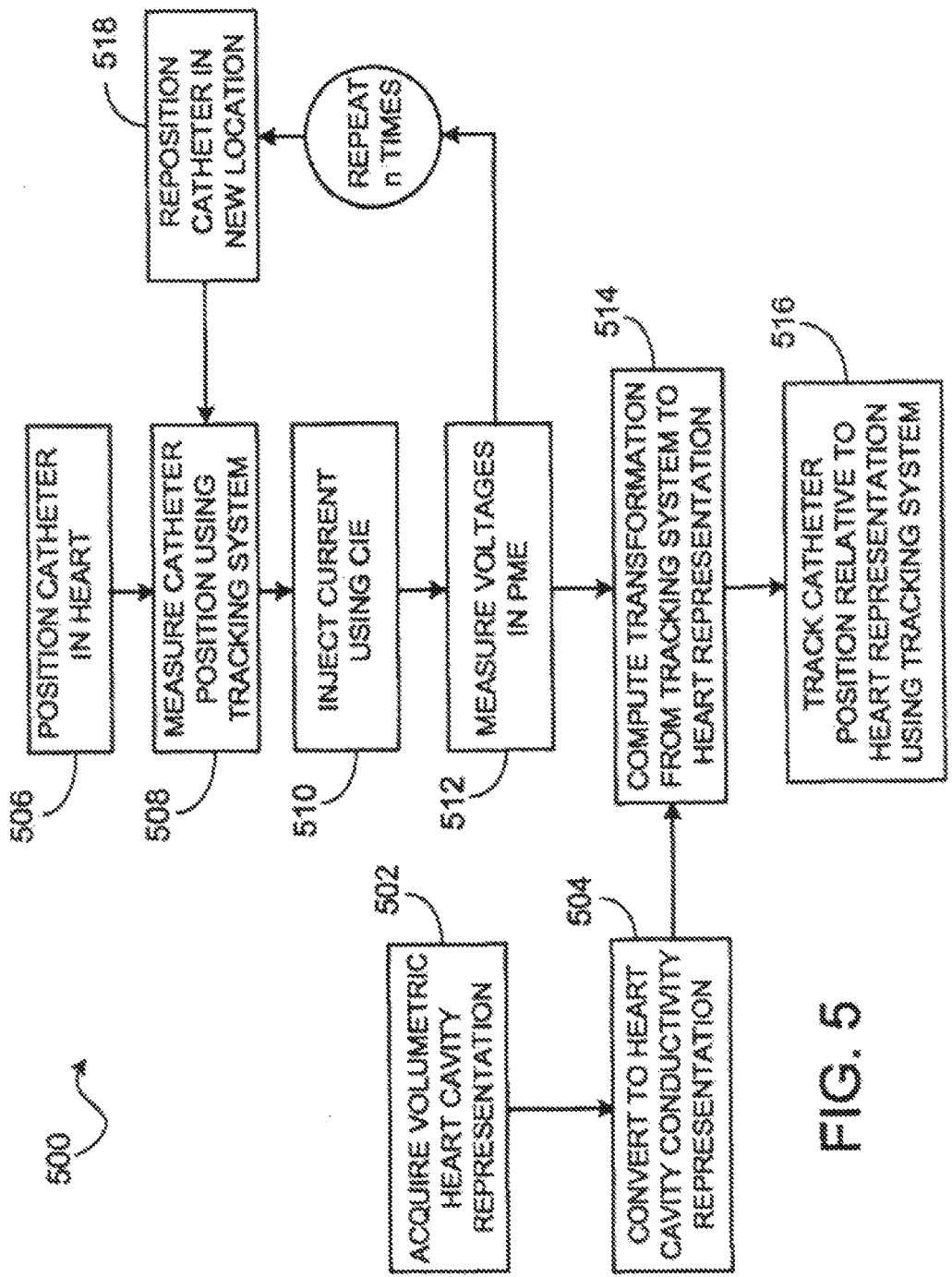
FIG. 5 is a flow diagram of an exemplary embodiment of an automatic registration procedure using an independent tracking system for the catheter.

FIG. 5 is a flow diagram providing a top-level depiction of the various procedures performed by the system 100 in the course of performing the automatic registration of the representation of the endocardium surface of the heart. In the embodiment shown in FIG. 5, the registration procedure is generally performed with the aid of an independent tracking system.

In step 506, catheter 110 is positioned in the heart cavity and in step 508 the position of the catheter is measured using the independent tracking system 180. In step 510, the CIEs are used to inject current into the heart cavity, and in step 512 the PMEs measure potentials in the heart cavity in response to the injected current. Although not explicitly depicted in FIG. 5, the steps 510 and 512 can be repeated for different combinations of the CIEs. Furthermore, as noted by step 518, the process can be repeated for different positions of the catheter, the relative positions of which can be tracked by independent tracking system 180. Details of these steps are described further below.

In a separate step, the registration system 100 obtains at step 502 the 3D image of the heart cavity (e.g., partial or complete anatomy of the patient's torso, including the patient's heart) from acquired volumetric cardiac representations of a patient's heart.

The volumetric representation may be acquired using a number of sources such as computed tomography (CT), magnetic resonance imaging (MRI), ultrasound, fluoroscopic rotational angiography, etc. In each imaging modality the patient may be injected with a contrast agent to enhance the boundary between tissue and blood. In addition, the volume is acquired over multiple phases of the heart's mechanical contraction. In order to obtain a particular phase of the mechanical contraction (e.g. end diastole), an ECG signal may be acquired in parallel in order to gate volume acquisition at the correct phase.

Figure 6:
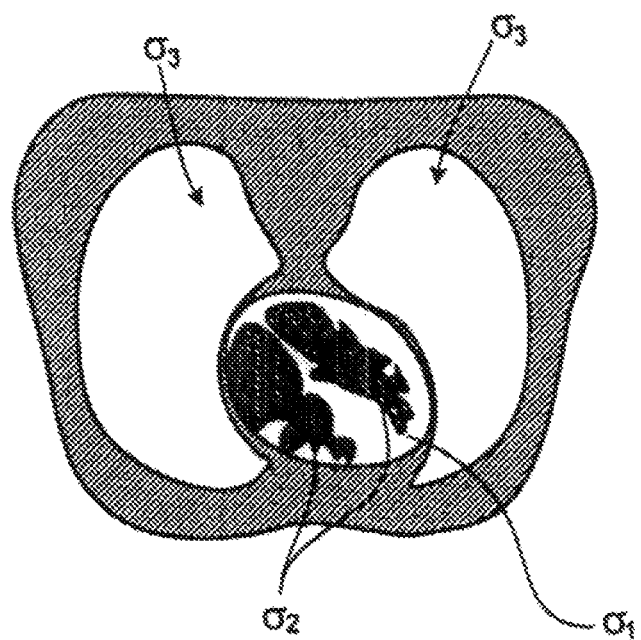
FIG. 6 is a schematic diagram of conductivities assigned to different structures in the heart cavity.

Various structures in the heart cavity are identified and delineated using a segmentation scheme. These structures include cardiac tissue and related vessels, blood, general torso tissue and lungs. After segmentation of the structures of interest, a choice is made regarding assigning of conductivity values to the structures of interest. Given suitable a-priori knowledge of the different characteristics of the conductivity of the medium in which the catheter 110 is inserted, as well as the surrounding structures, the conductivities can be assigned prior to the registrations process. Specifically, the respective conductivity values (or, equivalently, the resistivity values) of the intracardiac blood (i.e., the blood occupying the heart chamber) and that of the cardiac muscle are substantially uniform throughout the endocardium surface. For example, the resistivity of the intracardiac blood is 1.6 Ωm and that of the myocardium averages 5.6 Ωm. The heart is surrounded by the lungs whose resistivity is assigned 15 Ωm. Other torso tissue is assumed to have a conductivity similar to cardiac muscle 5.6 Ωm. Thus, the conductivity, or resistivity values of the blood and/or cardiac muscles for the particular patient with respect to which cardiac mapping is to be performed can be determined in advance, and these determined values can be used to perform the registration procedure, as described herein. FIG. 6 is an illustration of respective conductivity values assigned to the various tissues and media. Thus, as shown, the myocardium is assigned a conductivity of $\sigma_1$, intracardiac blood is assigned a conductivity of $\sigma_2$ and the lungs are assigned a conductivity $\sigma_3$.

However, in the absence of this a-priori knowledge, the conductivities of the structures of interest can be determined as part of the registration process. For the embodiment described herein, we consider the case that includes a-priori knowledge of the conductivity structure. It is recognized, however, that in the absence of this knowledge, the optimization problem would simply contain additional model parameters that describe the conductivity of the various structures of interest. Thus, solving for the additional conductivity parameters as part of the registration process can be done in a similar manner to the embodiment described herein.

Turning back to FIG. 5, having generated the 3D representation of the heart cavity and assigned, at step 504, appropriate electrical conductivity values, determination of the location of catheter 110 with respect to the generated 3D representation of the heart cavity is performed. This is accomplished by comparing observed values of electrical signals measured in step 512 to computed values (i.e., theoretical values) of those signals based on the heart cavity conductivity representation. Particularly, the measured potential field due to an input current from a dipole source is related via the conductivity structure of the medium by the continuous form of Ohm's law:

$$\nabla \cdot -\sigma \nabla \phi = I(\delta(r-r_{s+}) - \delta(r-r_{s-})) \quad (1)$$

Equation 1 is the partial differential equation that relates the potential field ($\phi$) to the input current (I), from a dipole, through the conductivity structure of the medium ($\sigma$). In Equation (1), $r_{s+}$ and $r_{s-}$ are the locations of the source and sink current sources, respectively, and $\delta(r-r_s)$ is the dirac delta function, centered at the current source or sink location. Thus, to compute the potential field φ, it is necessary to know the conductivity values (denoted σ) in the medium in which the potential field is computed.

With regard to step 506, the catheter 110 is typically inserted into the heart chamber via a suitable blood vessel leading to the heart chamber. In some embodiments, the electrodes of the catheter 110 are bundled into a compact configuration that enables the catheter 110 to be delivered to the heart chamber with minimal obstruction. Once inside the heart chamber, the electrodes of the catheter are deployed into a specified electrode arrangement relative to the catheter 110.

With the catheter 110 inserted into the patient's heart chamber and placed into a particular position within the heart chamber, information about the particular position can next be determined using the CIEs and PMEs disposed on the catheter 110. A pair of CIEs is selected as a source/sink pair by electronics module 140 to inject current into the heart cavity. One of the electrodes of the selected pair serves as the source electrode, and accordingly that electrode is activated by applying a voltage source to the source electrode. The other electrode serves as the sink electrode, and is thus set to a lower potential level than the source electrode. The other sink/source electrodes disposed on the catheter 110 are electrically deactivated and held at high impedance.

Figure 7:
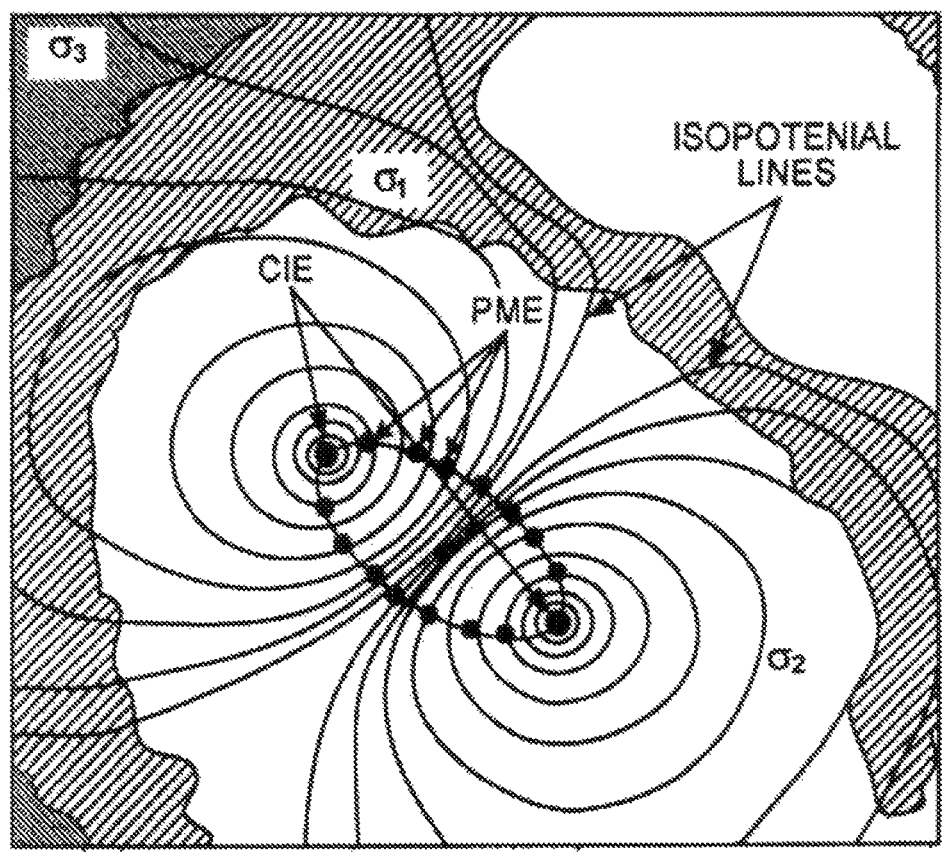
FIG. 7 is a schematic diagram of potential field lines produced by current injection electrodes (CIE) activated in a patient's heart cavity, and potential measuring electrodes on a catheter used to measure the potential field at different locations to infer information about the position of the catheter within the heart cavity.

The selected pair of source/sink electrode thus becomes active and imparts current, at step 510, into the intracardiac blood medium in which the catheter 110 is disposed. As shown in FIG. 7, causing a current to flow in the distribution of materials constituting the medium in which the catheter is disposed (in this case, the intracardiac blood) results in the formation of potential fields in the medium.

In response to current flow between the pair of selected source/sink electrodes, the PMEs distributed at multiple locations on the catheter 110 measure, at step 512, the resultant potential field present at the those multiple locations. The measured potentials are recorded, along with other information associated with the measurement, including, for example, the identity and/or location of the activated sink/source electrodes that imparted the current through the medium. Additionally, the location of the catheter 110 in relation to the coordinate system of the independent tracking system 180 is likewise recorded at step 508.

After the measurement of the potential fields caused by the activated source/sink electrodes has been completed and recorded, the pair of source/sink electrodes is de-activated, and another pair of source/sink electrodes is subsequently activated to cause potential fields corresponding to the next activated pair of source/sink electrodes to form. Although a new pair combination of electrodes is selected and activated, so as to cause an electric field that is different from the potential field previously formed, one of the electrodes may be an electrode that was previously selected in a preceding source/sink electrode pair selection.

The number of different source/sink electrode pair combinations that may used for any one given location of the catheter 110 depends on the desired balance between accuracy and robustness of the measurement to determine the positional information of the catheter 110, and the computation complexity and volume of data that can be handled, as well as the processing time required to process the acquired data and compute the desired positional information.

In one embodiment, each source/sink pair generates an oscillating current of 1 mA at 10 kHz while the switching between different pairs occurs at 100 Hz. It would be appreciated that other values of current amplitude, frequency and switching frequency may be used. The amount of current is chosen such that it is sufficient for signal detection, but low enough such that it does not affect cardiac tissue. The frequency is chosen such that it is high enough so that it can easily be filtered from the intracardiac signals (which are typically <2 kHz), and low enough so as to minimize cross talk between PME signals. The switching frequency between pairs is chosen such that multiple scans of all pairs can be accomplished while the heart may be assumed to be in a stable mechanical configuration (~100 mS). In the case of 100 Hz switching and three source/sink pairs, at least 3 scans of all pairs may be accomplished while the heart is in a stable mechanical configuration.

Figure 13:
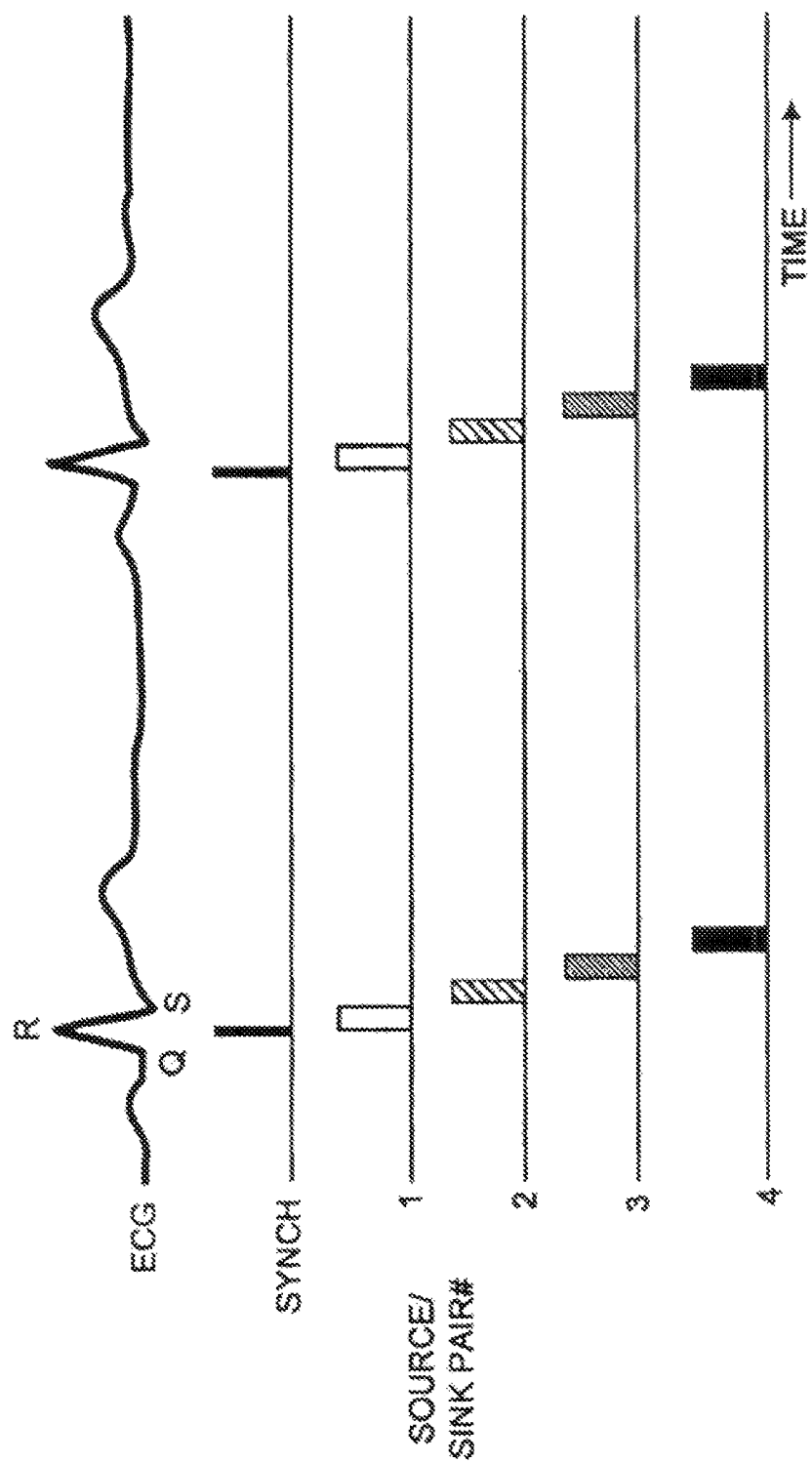
FIG. 13 is a schematic diagram of a timing sequence for synchronizing operation of the current injecting electrodes with the heart cycle.

Since the heart beats during the automatic registration process, it is preferable to perform the steps 508, 510, and 512 while the heart is in a mechanical cycle corresponding to the one represented by conductivity representation 504. In certain embodiments, ECG gating can be used to control the timing of the activation of the CIEs. Initially, an alignment algorithm is employed to detect the R wave from the ECG signal. Following a delay, each source/sink pair is activated in sequence. FIG. 13 shows the timing for a sequence of 4 CIE pairs. The initial delay is adjustable and is used to align the timing of the R wave with that of the mechanical phase in the chamber of interest. The four CIE pairs are then activated in sequence over a time period that is small relative to the period of the heart cycle.

Instead of ECG, other signals may be used to synchronize on the heart's mechanical contraction. For examples, the signals measured by the PME's at the frequency injected by the CIE continuously throughout the heart's cycle may be used in a manner similar to a conductance catheter or plethysmograph used to detect stroke volume. More specifically, the signal represented by $$S(t) = \sqrt{\sum_{n=1}^{N} (PME_n(t))^2}$$

where N is the number of PME's may be used for the synchronization. The amplitude of the PME signals that result from the injected CIE current is modulated by the heart's contraction due to the conductivity contrast between myocardium and blood. This modulation is synchronized with the heart's mechanical contraction. Signal S(t) may be used to in a manner identical to ECG gating shown in FIG. 13.

Other signals such as intracardiac electrograms, and pressure can also be used to synchronize on the heart's mechanical contraction.

In other embodiments, the potential field inside the patient's heart chamber may be created by having more than two CIEs activated simultaneously. For example, in some circumstances, two or more CIEs may be simultaneously coupled to signal sources as described in FIG. 4 to cause those two or more electrodes to inject current into the intracardiac blood in which the catheter 110 is disposed. In addition, in yet other embodiments multiple orthogonal frequencies may be introduced simultaneously in multiple electrodes.

Once measurements of the various potential fields resulting from activation of one or more source/sink electrode pairs at a particular location of the catheter 110 have been completed, the catheter 110 is moved, at step 518, to a new location within the heart chamber. At the new location of the catheter 110, a sequential activation of source/sink electrode pair is performed again, thus repeating the sequence of operation discussed above in relation to 508, 510 and 512. As a result, the potential fields formed by the source/sink electrodes of the catheter 110 and measured by the PMEs is performed at multiple locations of the catheter within the heart chamber. The displacement of the catheter 110 to multiple locations within the heart chamber and the subsequent sequence of measurement performed at each of those location effectively results in the implementation of a mega catheter having a number of electrodes that is proportional to the product of the actual number of physical electrodes mounted on the catheter and the number of locations to which the catheter is moved. In some embodiments, the sequence of source/sink electrode pair activations is constant such that at every location the same pairs of electrodes are activated, at the same order of activation. However, different activation sequences for the pairs of source/sink electrodes at different locations of the catheter 110 within the heart chamber may be implemented.

Once measurements of the potential fields for different CIE pair combinations and/or at different locations of the catheter 110 inside the heart chamber have been performed, an optimization routine (e.g., non-linear optimization routine) is applied, at step 514, to the sets of recorded measurements to determine the position of the catheter 110 relative to the 3D representation of the endocardium surface. Specifically, the optimization procedure applied at step 514 seeks to find the electrode positions within the heart cavity that minimized the alignment error between the observed potential values measured, by the PMEs, and the theoretically derived potential values.

In order to formulate the optimization problem, we first define the vector form of Equation 1:

$$(D \cdot S(\sigma) \cdot G)u = A(\sigma)u = q. \quad (2)$$

In Equation (2), D and G are matrices representing 3D divergence and gradient operators, respectively, $S(\sigma)$ is a matrix containing the conductivity values, u is a vector containing the potentials, $A(\sigma)$ is the complete forward operator matrix and q is a vector containing the locations of the positive and negative current sources. Although the location of the CIEs with respect to the independent tracking system is known, the locations of those electrodes with respect to the coordinate system of the 3D representation of the heart cavity is not known, and thus needs to be determined.

It is to be noted that the above formulation expressed in Equation (2) is a differential equation formulation of the forward problem. However, the forward problem can also be solved using an integral equation solution, and thus in some embodiments the desired results may be obtained using integral equation solutions. As described herein, the optimization problem will be explained in terms of using a differential formulation for the forward problem.

As can be seen from Equation (2), the theoretical potentials, for the given conductivity model assigned at step 504, can be determined according to:

$$u = A(\sigma)^{-1} q. \quad (3)$$

Equation (3) yields the potential everywhere in the 3D volume defined by the 3D representation of the heart cavity, and therefore provides the theoretical potentials in the heart cavity's frame of reference for a given location of the CIEs. However, because the actual measured data against which the optimization procedure will be performed corresponds to a small subset of potentials (namely, the potential measured at the limited number of PME locations), the set of theoretical potential values can be reduced to a subset of the available computed theoretical potentials. Accordingly, a projection matrix, Q, is defined for selecting data points from the volume, for particular locations inside the volume. Those particular locations associated with the projection matrix Q correspond to the PME locations that measure the potential fields created by injecting current using the CIEs. Applying the matrix Q to the vector u representing all the potential over the entire volume of the 3D representation of the heart cavity yields the following equation for expressing a subset of potential values at specific catheter locations:

$$d = Qu = QA(\sigma)^{-1} q. \quad (4)$$

The term d in Equation (4) represents the theoretical data at the limited number of locations corresponding to the PMEs. The locations of the catheter's electrodes, as used in the Q term are defined with respect to the external frame of reference (namely, the frame of reference of independent tracking system 180), which is denoted $\Omega_e$. The frame of reference of the 3D representation of the heart cavity is denoted $\Omega_I$. For convenience, the origin of the 3D representation of the heart cavity representation's frame of reference, $\Omega_I$, is defined as the centroid of the chamber of interest.

Figure 8A:
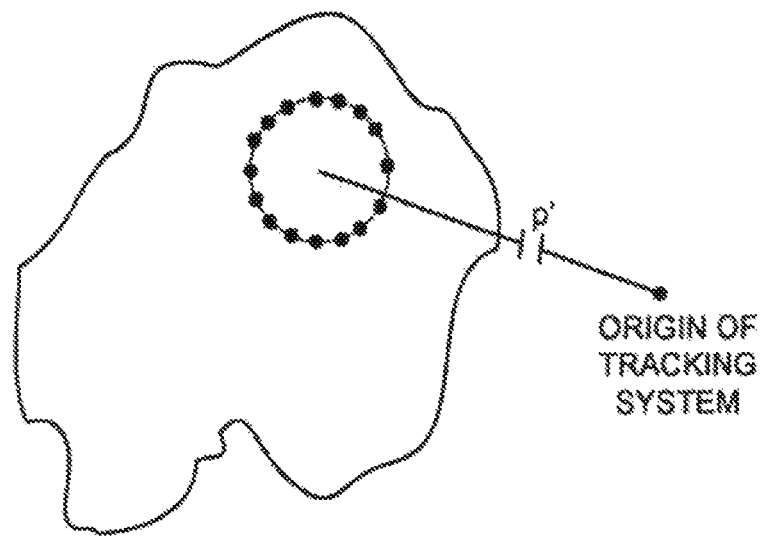
FIGS. 8a and 8b are exemplary illustrations of electrode measurements taken at a single catheter location (FIG. 8a) and at multiple catheter locations (FIG. 8b).
Figure 8B:
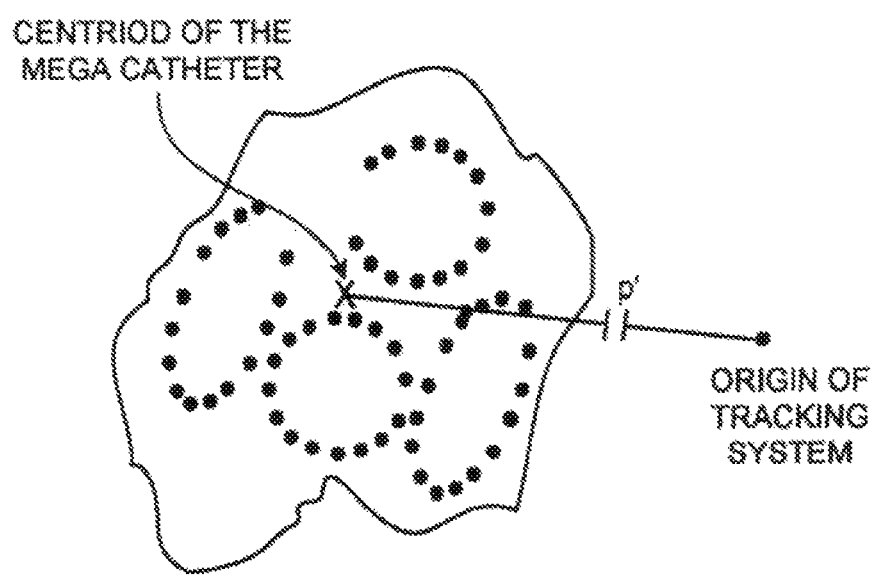

As noted, the data set that was obtained at the iterative measurements performed at steps 508, 510, and 512 is a composite of the potential field measurements performed at multiple catheter locations. As previously explained, obtaining measurements at multiple catheter locations within the heart chamber is effectively equivalent to having a mega catheter having a number of electrodes that is proportional to the product of the number of actual physical electrodes and the number of locations to which the catheter is moved. Moreover, the relative changes in catheter position can be tracked by independent tracking system 180. Thus, to register the 3D representation of the endocardium surface with respect to all of these data sets simultaneously, the data sets obtained at those multiple locations are viewed as data measurements from a single experiment ostensibly performed by a single, giant catheter. FIGS. 8a-b are illustrations of electrode measurements taken at a single (FIG. 8a) and multiple (FIG. 8b) catheter locations, respectively. The accuracy of the optimization procedure performed on measurements obtained from a single catheter location is affected by the number, and spatial span, of the electrodes partaking in the measurement process, and therefore the accuracy of the optimization procedure may be susceptible to measurement errors. On the other hand, when the catheter 110 is moved to multiple locations, the effective number of electrodes partaking in the measurement process and the spatial span of the measurements taken are increased, thereby improving the accuracy of the optimization.

To use all the data simultaneously, another coordinate system, denoted $\Omega_c$, is defined for the catheter, where a given electrode location is defined as follows:

$$r_{c_i} = r_{e_i} - \bar{r}_{e_i} \quad (5)$$

Where $\bar{r}_{e_i}$ is the location of the centroid corresponding to the composite of all the measurements taken at the various catheter locations. Given this new coordinate system, a corresponding projection matrix, $\tilde{Q}(r_i, \phi, \theta, \gamma)$, is defined in which $r_i$ is the location of the centroid of the mega catheter measured in the $\Omega_i$ frame of reference. $\phi$, $\theta$ and $\gamma$ denote the yaw, pitch and roll, respectively, of the virtual mega catheter with respect to the $\Omega_i$ frame of reference (i.e., the coordinate system of the 3D representation of the endocardium surface). Additionally, a new source vector, $\tilde{q}(r_i, \phi, \theta, \gamma)$, corresponding to the new coordinate system, $\Omega_c$, is also defined. Having defined the new coordinate system, $\Omega_c$, for the virtual mega catheter, Equation (4) can thus be expressed as follows:

$$d(m) = d(r_i, \phi, \theta, \gamma) = \tilde{Q} A(\sigma)^{-1} \tilde{q} \quad (6)$$

Equation (6) yields the computed theoretical potential values data as a function of the mega catheter's location with respect the 3D representation of the endocardium surface's frame of reference. It is to be noted that another equivalent formulation of the relationship between the measured potential field values and the computed theoretical values would be to consider the mega catheter as fixed, and view the conductivity matrix, S, as a function of m. Both these equivalent formulations would produce the same results.

Given equation (6) we can define an objective function, $\Phi(m)$, that enables the determination of m, and consequently the location of the mega catheter with respect to the 3D endocardium surface representation:

$$\Phi(m) = \|d(m) - d_{obs}\|^2 \tag{7}$$

where $d_{obs}$ is the vector of observed potential field data measured by the electrodes of the catheter. In this case, the vector of observed data corresponds to the separate measurements performed for each of the CIE pairs that were sequentially activated to generate corresponding potential fields inside the intracardiac blood medium. The observed data pertains to measurements performed by the mega catheter (i.e., over the multiple locations to which the catheter 110 was displaced during the course of conducting the measurements), and not merely by the catheter positioned in a single location of the catheter. It should be again noted that what enables measurements from the mega catheter to be used as opposed to measurements from a single catheter location is the fact that the independent tracking system 180 is employed, which enables the relative positions of the catheter 110 with respect to the various locations to which the catheter 110 is displaced to be determined.

By minimizing equation (7), a model, m, is determined that leads to the best fit of the observed data (i.e., the measured potential fields) in a least-squares sense. While the above optimization is cast in terms of minimizing the $L_2$ norm of the residuals, i.e., the sum of the squares, other error metrics may be used to perform the best fit of the observed data to the theoretical data, such as any standard $L_n$ norm or a modified norm such as the Huber norm.

Solution of Equation (7) yields the locations of the mega catheter electrodes, with respect to the frame of reference of the 3D representation of the endocardium surface, that result in the best fit between the theoretical data and the observed data. As will become apparent below, with these electrode location values now determined, the transformation parameters to transform coordinates in the frame of reference of independent tracking system 180 to the frame of reference of the 3D representation of the endocardium surface may subsequently be computed.

Minimizing Equation (7) requires a non-linear optimization approach. There are multiple techniques that may be used to arrive at a solution. In general there are two classes of techniques that may be used: stochastic and deterministic. Stochastic optimization techniques, such as simulated annealing and genetic algorithms, involve stochastically guided searches of the model space to find a suitable minimum. Deterministic approaches, such as Gauss-Newton approach, Levenberg-Marquardt approach and the Newton method, involve solving a linearized version of the non-linear problem multiple times in order to achieve a suitable solution.

For illustration purposes, described herein is as an example of a deterministic approach, namely, the Gauss-Newton approach, which can be used to solve Equation (7). However, other non-linear solution techniques may be used to solve the above optimization problem.

Given the objective function defined Equation (7), the Gauss-Newton approach is used to identify the model that leads to the best fit of the observed data to the theoretical data. A starting guess, $m_i$, is first defined. In practice, this starting guess would usually be a vector of zeros. Equation (7) is then linearized about this model to yield:

$$\Phi(m) = \frac{1}{2}\left\|\left(d + \frac{\partial d}{\partial m}.\delta m\right) - d_{obs}\right\|^2 \tag{8}$$

To obtain the minimum of Equation (8), the derivative with respect to the model is taken, and set it to zero. This yields the following Gauss-Newton equation:

$$\underbrace{(J^T J)}_{H} \cdot \delta m = -\underbrace{\left(J^T\left(\tilde{Q}A^{-1}\overline{q} - d_{obs}\right)\right)}_{g} \tag{9}$$

where J is the Jacobian, or sensitivity matrix, $$\left(\frac{\partial d_i}{\partial m_j}\right),$$

g is the gradient of the objective function, and H is the approximation to the Hessian. Equation (9) is solved to yield the so-called model-update, $\delta m$, which represents an incremental change in the model, which decreases the value of the objective function. The model-update is then used to generate a new model:

$$m_{i+1} = m_i + \delta m \tag{10}$$

where $m_{i+1}$ is the new model.

Because Equation (9) resulted from a linearization about the model, $m_i$, the resulting model, $m_{i+1}$, is likely not the local minimum of Equation (7). Therefore, another Gauss-Newton iteration is performed, this time, linearizing Equation (7) about the model $m_{i+1}$. This iterative process is repeated until the objective function has decreased to the noise level of the data.

Aligning the mega catheter with the 3D representation of the endocardium surface image is done by applying the following transform:

$$r_i = R \Box r_c + \Delta r \tag{11}$$

where $r_i$ and $r_c$ are coordinates in the $\Omega_i$ and $\Omega_c$ reference frames, $\Delta r$ is the translation vector that can be derived from m, where $m = (\Delta r, \phi, \theta, \gamma)$, and R is the Euler rotation matrix defined as follows:

$$R = B \cdot C \cdot D \tag{12}$$

where:

$$B = \begin{bmatrix} 1 & 0 & 0 \\ 0 & \cos\gamma & \sin\gamma \\ 0 & -\sin\gamma & \cos\gamma \end{bmatrix};$$

$$C = \begin{bmatrix} \cos\theta & 0 & -\sin\theta \\ 0 & 1 & 0 \\ \sin\theta & 0 & \cos\theta \end{bmatrix};$$

$$D = \begin{bmatrix} \cos\phi & \sin\phi & 0 \\ \sin\phi & \cos\phi & 0 \\ 0 & 0 & 1 \end{bmatrix}$$

Following the application of equation (11), the coordinates of each catheter electrode in the $\Omega_i$ reference frame (i.e., the reference frame of the 3D representation of the endocardium surface) are determined from the catheter's electrodes' coordinates in the $\Omega_c$. As previously explained, the catheter coordinates in the $\Omega_c$ frame of reference are determined using the coordinates of the catheter in the $\Omega_e$ frame of reference (i.e., the frame of reference of the tracking system) using, for example, Equation (5).

As noted, the procedure described in relation to Equations (7)-(11) yields the locations of the electrodes of the mega catheter with respect the frame of reference of the 3D representation of endocardium surface, and thus enables aligning the catheter's frame of reference with the frame of reference of the 3D representation of the endocardium surface with respect to the catheter current location (or, more specifically, with respect to the constellation of measurements obtained from the mega catheter). The next stage of the automatic registration process involves calculating the transform between $\Omega_i$ and $\Omega_e$ so that the coordinates of the catheter 110 in the frame of reference of the 3D representation of the endocardium surface can be obtained from knowledge of the current coordinates of the catheter 110 as indicated by the independent tracking system 180. The objective function for registering the two data sets can be described as follows:

$$\Psi(r, \Delta r) = \min_{R,\Delta r} \|r_e - R \cdot r_i - \Delta r\|^2 \quad (13)$$

where $r_i$ and $r_e$ are coordinates in the $\Omega_i$ and $\Omega_e$ reference frames. Once again, $\Delta r$ is the translation vector and R is the Euler rotation matrix. Unlike equation (11), where R and $\Delta r$ were known, Equation (13) seeks to find the R and $\Delta r$ that minimize the expression provided in Equation (13).

This optimization problem can also be solved using a variety of non-linear optimization techniques. As an illustrative example follows.

Firstly, the two sets of coordinates, $r_i$ and $r_e$ presented in Equation (5) are modified so that the origin of the each point cloud is the centroid of the point cloud. Thus, Equation (13) can be re-written as:

$$\Psi(R) = \min_R \|\tilde{r}_e - R \cdot \tilde{r}_i\|^2 \quad (14)$$

where $\tilde{r}_e$ and $\tilde{r}_i$ are the point cloud coordinates, shifted about their respective centroids.

Accordingly, at step 514 of procedure 500, the coordinates of multiple catheter locations, determined during the multiple iterations performed with respect to 508, 510, and—512 of procedure 500, are provided. These coordinates are provided both in terms of the frame of reference of the independent tracking system and in terms of the frame of reference of the 3D representation of the heart cavity (as provided by step 504 of procedure 500). With these coincident point clouds of catheter locations provided in terms of the frame of reference of the independent tracking system and the frame of reference of the 3D representation of the heart cavity, the rotational matrix R that minimizes the difference between $R \cdot \tilde{r}_i$ and $\tilde{r}_e$ is determined. The optimal solution to equation (14) can be determined using the singular value decomposition (SVD) of the correlation matrix between $\tilde{r}_e$ and $\tilde{r}_i$. The correlation matrix is defined as:

$$H = \tilde{r}_i \cdot \tilde{r}_e^T \quad (15)$$

Using the notation of $H = U \Lambda V^T$ for the SVD, the optimal solution for R is thus presented as:

$$R = V \cdot U^T \quad (16)$$

Once R has been obtained, $\Delta r$ is computed as:

$$\Delta r = \bar{r}_e - R \cdot \bar{r}_i \quad (17)$$

Where $\bar{r}_e$ and $\bar{r}_i$ are the locations of the centroids of the two respective point clouds. Because R and $\Delta r$ are now known, Equation (11) is applied to the coordinates of the 3D representation of the endocardium surface to yield the new series of coordinates in the $\Omega_e$ reference frame of the independent tracking system. The independent tracking system can now be used to track the catheter with respect to a visual representation of the heart, and obtain, at step 516, successive catheter locations of catheter 110 in terms of the 3D representation of the heart cavity given the coordinates of the catheter as indicated by the independent tracking system 180. It should be noted the frame of reference transformation can be performed in the opposite direction, i.e., projecting from $\Omega_e$ to $\Omega_i$. One drawback of such an approach is that every time the catheter 110 is moved, Equation (11) must be applied to the catheter location. However this is an instantaneous calculation, so in practice either approach would be suitable.

Catheter Tracking without Independent Tracking System

Figure 9:
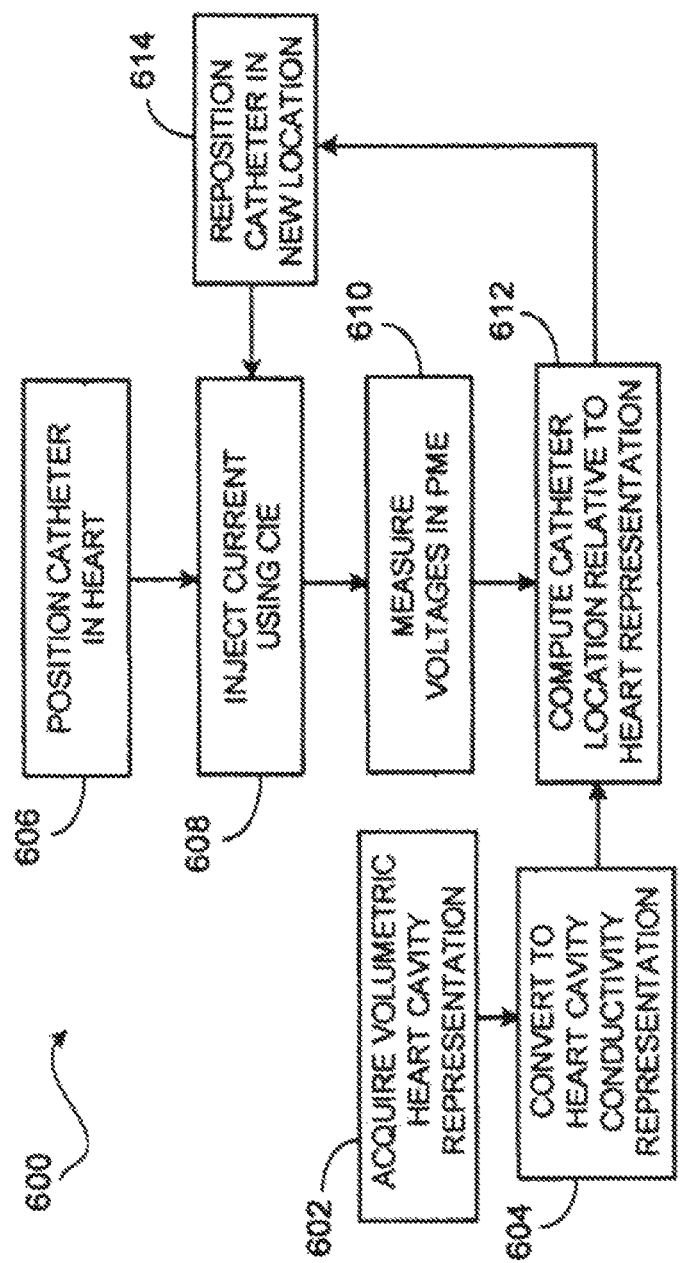
FIG. 9 is a flow diagram of another exemplary embodiment of a registration procedure for determining the position of a catheter in a patient's heart cavity.

FIG. 9 is a flow diagram of another exemplary embodiment of a registration procedure 600 that is performed without using any independent tracking system. Because the tracking system is not utilized, the positions of spatial locations of the catheter 110 relative to each other cannot be ascertained. In other words, without a tracking system to track the relative movement of the catheter 110, no information is available on the distance and direction that the catheter 110 moved from a first position to a second position inside the heart chamber. Accordingly, because relative positions of the catheter with respect to different locations in the heart chamber cannot be directly determined (i.e., without having to perform optimization computations), an approach that uses a composite of measurements taken at different locations of the catheter 110, as was performed in relation to procedure 500, is not used. Consequently, while the spatial positioning of the catheter 110 with respect to the coordinate system of the 3D representation of the heart cavity can be determined for a particular location, once the catheter 110 is moved to a different location within the heart chamber, the procedure 600 has to be performed anew to determine the spatial positioning of the new location of the catheter 110 relative to the 3D representation of the heart cavity This approach has the advantage of negating the need for additional equipment (i.e., the independent tracking system).

Particularly, as shown in FIG. 9, a 3D representation of the patient's heart cavity is constructed, at step 602, from volumetric data in a manner similar to that outlined with respect to the construction of the 3D representation performed at step 502 of procedure 500. The conductivity values at various locations of the constructed 3D representation of the heart cavity for various tissues are then assigned at step 604 in a manner similar to the conductivity assignment performed at step 504 of procedure 500.

At step 606, the catheter 110 is inserted into the patient's heart chamber, and the catheter 110 is moved to some unknown position. Subsequently, at step 608 the control mechanism of electronics module 140 commences an activation sequence of the CIEs of the catheter 110 to cause current injection into the intracardiac blood medium in which the catheter 110 is disposed, in a manner similar to that performed at 510 of procedure 500. Here too, the control mechanism, or alternatively, the operator of system 100, causes current to be injected in an ordered sequential manner. Consequently, potential fields, corresponding to the various source/sink electrode configurations activated, are formed inside the patient's heart chamber.

The PMEs of the catheter 110 measure, at 610, the potential fields present at the electrodes' positions, and the measured potentials are amplified and sampled by the electronics module 140 of system 100. Thus, at the catheter's position inside the patient's heart chamber, multiple sets of potential field measurements, corresponding to the respective source/sink electrode configurations that were activated to create those potential fields, are recorded and constitute the observed raw data that subsequently is used to determine the location of the catheter 110 relative to 3D representation of the heart cavity.

Accordingly, as further shown in FIG. 9, at step 612 the measured potentials are processed by an optimization routine, such as any one of the various non-linear technique that may be used with respect to the non-linear optimization techniques performed in procedure 500, to determine the position of the catheter 110 with respect to the 3D representation of the heart cavity. The processing operation and optimization procedure performed by procedure 600 at step 612 are similar to the operations described above in relation to Equations (6)-(12). Briefly, an objective function is defined that searches for the coordinates of the catheter 110 (and by extension, the coordinates of the electrodes mounted on the catheter) with respect to the 3D representation of the heart cavity, that would provide the best fit match between the observed data sets of the potential measurements (i.e., for each of activated CIE) and the corresponding theoretical potential values.

Particularly, the theoretical potential values at the electrodes used to measure the potential field created in the heart chamber as a result of the current injected by activated source/sink electrodes can be expressed as:

$$d(m) = d(r_i, \phi, \theta, \gamma) = \tilde{Q}A(\sigma)^{-1}\tilde{q} \quad (18)$$

Figure 10:
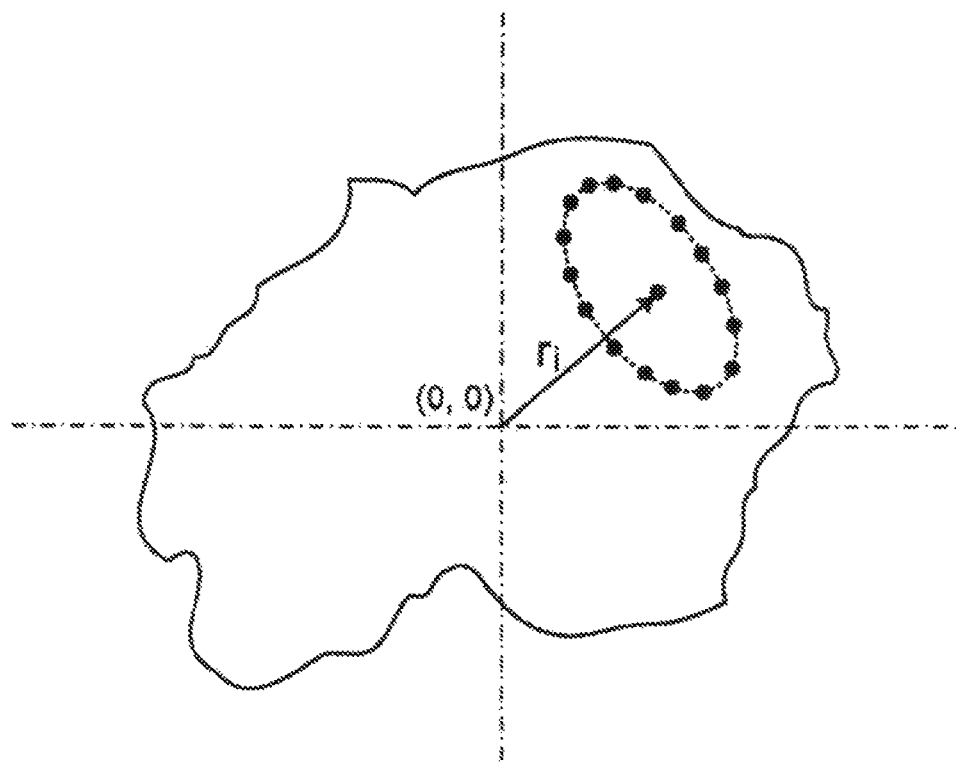
FIG. 10 is exemplary illustration of electrode measurements taken at a single catheter location.

In the projection matrix, $\tilde{Q}(r_i, \phi, \theta, \gamma)$, $r_i$ is location of the centroid of the catheter measured in the $\Omega_i$ frame of reference. $\phi$, $\theta$ and $\gamma$ denote the yaw, pitch and roll, respectively, of the catheter 110 with respect to the $\Omega_i$ frame of reference. The source vector, $\tilde{q}(r_i, \phi, \theta, \gamma)$, corresponds to the locations of the source/sink electrodes injecting the current relative to the centroid $r_i$. FIG. 10 shows a schematic representation of the locations of the electrodes relative to the origin of the frame of reference of the 3D representation of the heart cavity, and relative to the centroid $r_i$ representing the center of the object on which the CIEs are mounted. Equation (18) yields the theoretical data as a function of the catheter location with respect to the frame of reference of the 3D representation of the heart cavity. As noted with respect to procedure 500, an equivalent formulation of the problem represented by Equation (18) would be to consider the catheter as fixed, and view the conductivity matrix, S, as a function of m. Under those circumstances, this alternative formulation would produce the same results as the formulation of Equation (18).

With the formulation of Equation (18), the objective function that will be used to determine the location of the catheter 110 with respect to the 3D representation of the heart cavity is defined as:

$$\Phi(m) = \|d(m) - d_{obs}\|^2 \quad (19)$$

By minimizing Equation (19), the model m that leads to the best fit of the observed data in a least-squares sense is determined. The optimization techniques that are applied to determining the best-fit model m are similar to those describe in relation to procedure 500.

After the procedure 600 has determined the position of the catheter 110 with respect to the 3D representation of the heart cavity, a cardiac mapping procedure performed using the catheter 110 can be performed, as described above. Upon the completion of the mapping procedure at the current location of the catheter 110, the catheter may be moved to a new location. Unlike procedure 500, which generates a transformation function that may be subsequently used at other catheter locations to determine the position of the catheter 110 relative to the 3D representation of the endocardium surface, once the catheter 110 is moved to a new location, the procedure 600 is repeated to determine the new location of the catheter 110.

Additional Electrode Configurations

Figure 11C:
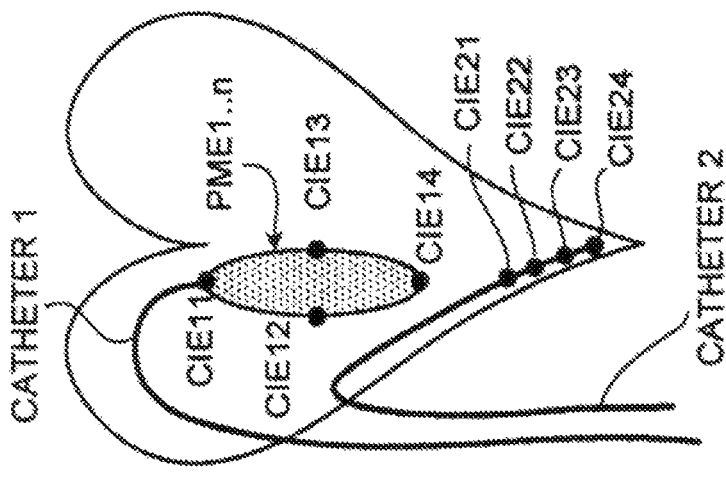
FIGS. 11a-c are exemplary schematic diagrams of different arrangements for positioning current injection electrodes (CIEs) and potential measuring electrodes (PMEs) with respect to a patient's heart cavity.
Figure 11B:
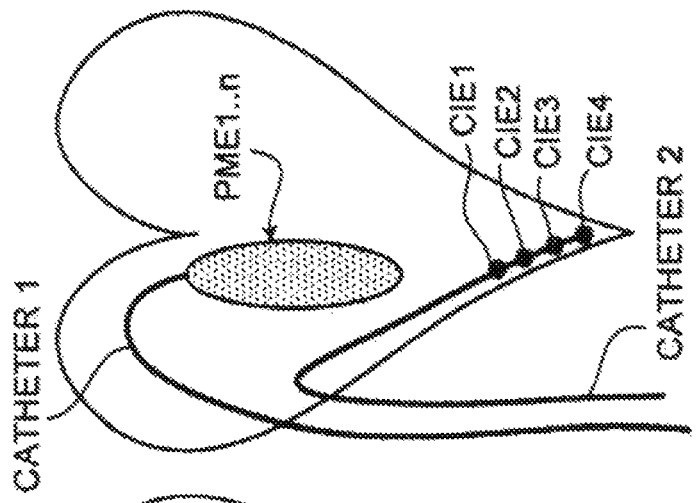
Figure 11A:
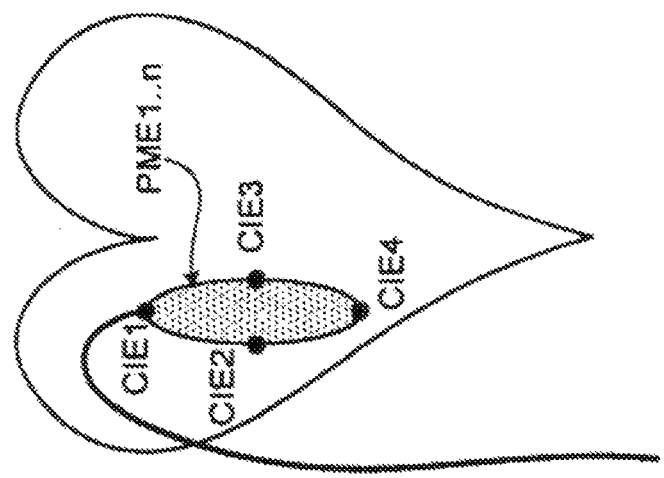

In the specific embodiments describe above, both the CIEs and PMEs are on the same catheter. Other configurations are also possible as shown in FIGS. 11a-c. For example, while FIG. 11a shows catheter 110a in a patients heart chamber 108 as having both CIEs (specifically, CIE1, CIE2, CIE3, and CIE4) and PMEs (specifically, PME 1 ... n), FIGS. 11b and 11c show configurations with two (2) catheters, the second of which is anchored within the heart so as not to move relative to the heart chamber and includes some or all of the CIEs, while the other catheter is movable and includes the PMEs (which may also be used for cardiac mapping).

Referring to FIG. 11b, the first movable catheter 110b includes the PMEs (specifically, PME 1 ... n), but not CIEs, all of which are located on the second catheter 111b, The second catheter may be anchored in structures such as the coronary sinus, atrial appendages, or a ventricular apex. The second catheter may be a linear catheter with CIEs spaced apart from each other along a linear line. The first catheter would contain all PME which would be distributed somewhat uniformly on a 3D surface.

Referring to FIG. 11c, the first movable catheter 110c includes all of the PMEs (which may also be used for cardiac mapping) and some of the CIEs (specifically CIE11, CIE12, CIE13, and CIE14), and the second catheter includes the remaining CIEs (specifically, CIE21, CIE22, CIE23, CIE24). Accordingly, source/sink electrode pairs may be used across the two catheters. In this manner one of the current injecting electrodes can anchored with respect to the heart while the other is moving. In general, the various electrode types may be mounted on multiple objects that are deployed in a heart chamber or surrounding structures. Moreover, in further embodiments, rather than injecting the currents using a second catheter (as in FIGS. 11b and 11c), cutaneous patches may be used on the body surface to inject current into the heart cavity from outside the heart cavity.

In yet further embodiments, one or more of the electrodes on the catheter can be driven by electronics module 140 to function as both a CIE and a PME. For example, when it is desired to use an electrode as both PME and CIE, the electrode is connected to both a signal acquisition module and a signal generation module. For example, for the electronics module depicted in FIG. 4, when the electrode is not used as a CIE to drive a current, the switch in the signal generation module corresponding to the respective electrode is opened. Accordingly, time division multiplexing schemes in the driving electronics of module 140 can be used to operate a given catheter electrode as either a CIE or a PME. In yet another example, the electronics module can drive a given electrode so that it functions as a CIE at high frequencies and a PME at low frequencies (such as might be useful for cardiac mapping.)

Complex Conductivity

As noted above, the measurements collected at the PMEs as a result of current injected by the CIE are generally affected by the complex conductivity, or admittivity, distribution of the medium. While the specific embodiment discussed above focus on the real part of the conductivity which affects the amplitude measured by the PMEs, additional information can also be obtained by accounting for the real part (conductivity) and imaginary part (permittivity) of the medium's complex conductivity, which affects the amplitude and phase of the signal measured by the PME. In this manner, the use of both amplitude and phase, or phase alone may also be used for tracking and/or automatic registration. Use of the imaginary part of the complex conductivity is of particular importance in material distributions where the permittivity contrast exceeds that of the conductivity contrast.

To modify the mathematical formalism for the specific embodiments described above to account for imaginary part of the complex conductivity, the forward problem expressed in Equation (1) is changed. Specifically, Equation (1) is modified as follows:

$$\nabla \cdot -\sigma^* \nabla \phi^* = I(\delta(r - r_{s+}) - \delta(r - r_{s-})). \tag{20}$$

where $\sigma^*$ and $\phi^*$ represent the complex conductivity and complex potential, respectively. The complex conductivity is defined as: $\sigma^* = \sigma + i\omega\epsilon$, where $\sigma$ is the real component of conductivity (as in Equation 1), $\omega$ is the frequency of the current source, and $\epsilon$ is the electrical permittivity. From Equation (20), one can obtain a corresponding discretized system, analogous to Equation (2), that accounts for the complex conductivity and potential. The optimization approaches described above can then be applied to this complex discretized system to perform the complex impedance registration.

Post Registration/Tracking Operation

Once the registration procedure is completed, the cardiac mapping (e.g., non-contact mapping) of electro-physiological information about the endocardium surface, as well as other post-registration operations may be performed. A description of the mapping and other post-operations procedures that may be performed are provided for example, in application Ser. No. 11/451,871, entitled "NON-CONTACT CARDIAC MAPPING, INCLUDING RESOLUTION MAP," and filed Jun. 13, 2006, the content of which is hereby incorporated by reference in its entirety, as well as application Ser. Nos. 11/451,898, and 11/451,908, referred to above.

Briefly, and with reference to FIG. 12, the catheter 110 may be moved to a first location within the heart chamber, at step 902, in which the first set of measurement by the catheter's multiple mapping electrodes is performed. Control of the catheter's movement and location within the heart chamber is performed manually by the operator manipulating the catheter 110. Alternatively, the movement of the catheter 110 within the heart chamber may be automated by use of techniques such as magnetic (see, e.g., Stereotaxis, Inc. of St. Louis, Mo.) or robotic (see, e.g., Hansen Robotics, Inc.) navigation. Catheter manipulation may be used to cause the catheter to follow a pre-determined displacement route to collect data at locations that may be considered to be of higher interest than others. For example, in some embodiments, the catheter 110 may be moved at specified displacement intervals in an area of the heart chamber that is known to have abnormal cardiac activity.

The 3D location of the catheter 110, and/or to its multiple electrodes, is then determined using one of the techniques discussed above. If a tracking system, such as the independent tracking system 180, is used, the coordinate system transformation function between the tracking system 180 frame of reference and the 3D representation of the heart cavity as determined, for example, at step 516 of procedure 500, is applied to the coordinates of the catheter 110 identified by the independent tracking system 180. If an independent tracking system is not used to facilitate determining the location of the catheter 110 in the patient's heart chamber, the location of the catheter 110 in relation to the 3D representation of the endocardium surface is determined by performing, for example, procedure 600 as described herein.

At its current location, the multiple mapping electrodes of the catheter 110 (which, as previously noted, may be the same as the PMEs used during the tracking process as implemented either through procedure 500 or procedure 600) acquire signals resulting from the heart's electrical activities (at 904).

The mapping system (which may be implemented using the same hardware used to implement registration system 100) generates reconstruction transformation functions, at step 906, to be applied on the acquired signals to reconstruct the electro-physiological information at the endocardium surface. The generated reconstruction transformation functions may be based, among other things, on pre-computed reconstruction transformation functions that were previously determined (generally prior to insertion of the catheter 110 into the patient's heart chamber), and the catheter's location relative to the endocardium surface. Thus, in some embodiments, for every location of the catheter 110 at which raw data is acquired, a corresponding set of reconstructed electro-physiological information is computed.

After the raw data corresponding to the heart's electrical activity has been acquired, recorded and processed using reconstruction transformation function(s) to obtain reconstructed electro-physiological information at the endocardium surface (also at step 906), a determination is made, at step 908, whether there are additional locations within the heart chamber to which the catheter 110 is to be moved. If there are additional locations in the heart chamber to which the catheter 110 needs to be moved the catheter is moved, using manual or automatic control, to the next location in the heart chamber, whereupon the operation described in relation to the steps 902-906 in FIG. 12 are performed for that next location.

To enhance the quality of the reconstructed electro-physiological information at the endocardium surface, in some embodiments the catheter 110 is moved to more than three locations (for example, more than 5, 10, or even 50 locations) within the heart chamber. Further, the spatial range over which the catheter is moved may be larger than one third (⅓) of the diameter of the heart cavity (for example, larger than 35%, 40%, 50% or even 60% of the diameter of the heart cavity).

In some embodiments, a composite set of electro-physiological information can be generated by selecting from multiple sets of reconstructed electro-physiological information portions of the reconstructed information. Selecting which portions of reconstructed information to use can be based on resolution maps that are indicative of the quality of the reconstructed information for a particular portion or set of the reconstructed electro-physiological information. Other criteria and techniques for selecting suitable portions of data to reconstruct a composite set of electro-physiological information may be used.

In some embodiments, one (or more) composite reconstruction transformation function is computed that is applied collectively to the raw data acquired at multiple locations to generate a resultant composite set of reconstructed electro-physiological information based on a substantial part of the data acquired. Such a transformation function represents a "mega transformation function" that corresponds to a "mega catheter," whose effective number of electrodes and electrode span is related to the number of locations to which the catheter was moved within the heart chamber. Under those circumstances the generation of the composite reconstruction transformation function is deferred until data is collected from the catheter's multiple locations.

Alternatively, in some embodiments, the "mega transformation function" and "mega catheter" may be updated on an ongoing basis to take into account a given relevant measurement window. This window may be a fixed number of measurements such that the arrival of new measurements displaces measurements that were obtained before the time window. This yields a constantly updating moving average.

In some embodiments, signals are measured throughout a heart beat cycle (for example, a measurement can be made at each catheter electrode at each of multiple, different phases of a single beat heart cycle).

Yet in further embodiments the reconstructed set of electro-physiological information is computed based on measurements taken over one or more heart beats. In the latter situation, the catheter is moved to a particular location, and acquires multiple sets of raw data over several heart beats. The acquired data is averaged, and the reconstruction process is applied to the averaged values. If the data is acquired over B heart beats (i.e., B measurements), an improvement in the signal-to-noise ratio proportional to $\sqrt{B}$ is obtained. The timing of the measurement operation is generally synchronized to ensure that measured data is acquired at approximately the same phase of the heart cycle.

If it is determined at 908 that there are no additional locations within the heart chamber at which data needs to be collected, then the non-contact mapping system may perform at 910 post-processing operations on the reconstructed electro-physiological information to extract clinically useful data. As noted, in some embodiments the mapping system produces a composite reconstructed set of electro-physiological information. Post processing operation are performed, under those circumstances, on the composite set of reconstructed electro-physiological information. In some circumstances where the non-contact mapping system produces multiple reconstructed sets of electro-physiological information for the raw data collected at each location in the heart chamber to which the catheter 110 was moved, the post processing operations are performed individually on one or more sets of reconstructed electro-physiological information.

In some embodiments, the post processing may involve nothing further then selecting a format for outputting (e.g., displaying) the reconstructed potentials to a user. In other embodiments, the post-processing may involve significant further mathematical manipulation of the reconstructed potentials to provide additional types of electro-physiological information.

The reconstructed electro-physiological information and/or sets of post-processed data are then displayed at 912. The information, be it the reconstructed electro-physiological information or any data resulting from the post-processing performed at 910, is displayed on a 3D graphical rendering of the 3D representation of the endocardium surface generated from the same data set acquired at 602 or at 502.

One of the post-processing operations performed on the reconstructed set(s) of electro-physiological information can include the generation of a resolution map. Such a resolution map indicates the spatial resolution of electro-physiological information at points on the endocardium surface, thereby providing a measure of the reliability and accuracy of the information at various points on the endocardium surface. The resolution map may also be used to form a composite set of reconstructed electro-physiological information by associating with individual sets of acquired raw data and/or individual sets of reconstructed electro-physiological information corresponding resolution maps. A resultant composite set is then formed by selecting portions of acquired raw data (or reconstructed information) whose reliability or accuracy, as indicated by the resolution map corresponding to the set from which the data is selected, is sufficiently high. Resolution maps may be used with any form of post-processing operation including all modes listed below. Strictly speaking, information about the resolution maps can be determined prior to obtaining the reconstructed potential data; however, herein we generally refer to the generation and display of the resolution map as "post-processing" because such information is typically presented to the user after at least some of the potentials are reconstructed.

Another type of post-processing operation that may be performed includes the generation of isopotential maps. Particularly, where the reconstructed electro-physiological information pertains to electrical potentials, the reconstructed potentials may be color coded and superimposed on the 3D endocardial representation. Isopotential maps are the reconstructed potentials computed for every sampled time instance for a set of data acquired over a single or multiple heart beats.

Yet another type of post-processing operation includes the generation of timing maps (such as activation time maps). The timing maps provide information on the time-dependent behavior of the heart's electrical activity. Particularly, the activation map indicates at what point in time particular points on the endocardium surface experience a change in their electrical activity. For example, the activation map could identify the point in time at which particular cells on the endocardium surface experienced depolarization. Another type of timing map may be an iso-duration map where the amount of time certain tissue has been active for is detected. Timing maps may be computed from the reconstructed potentials over a single or multiple heart beats. Timing maps may be determined and displayed for one or more points on the endocardium surface representation.

Another type of post processing operation that may be performed at 910 is the to generation of voltage maps. Voltage maps can be used to display characteristics of voltage amplitude in a given area. The voltage maps may be computed from the reconstructed potentials over a single or multiple heart beats. Useful voltage map information that may be determined and displayed for one or more points on the endocardium surface representation includes the maximum amplitude, or root mean square potential values.

Another type of post-processing operation is the generation of a difference map. The difference map provides information regarding the effectiveness of the clinical procedure (e.g., ablation) performed on the patient to ameliorate the symptoms of arrhythmias. The difference map compares the electrical behavior of the heart, as reflected from two or more voltage maps generated before and after the performance of the particular clinical procedure.

A further type of post processing operation is the generation of frequency maps. Frequency mapping, and more generally spectral analysis, are used to identify on the endocardium surface localized sites of high-frequency activity during fibrillation. Frequency maps are computed by acquiring multiple sets of reconstructed information over a particular time interval which includes a single or multiple heart beats. The acquired raw data is then used to obtain the frequency representation of that data. Specific information (e.g., dominant frequency components) from the frequency representation is subsequently identified, and that identified information may be displayed.

Other types of post-processing information may likewise be performed at 910.

Other Embodiments

The methods and systems described herein are not limited to a particular hardware or software configuration, and may find applicability in many computing or processing environments. The methods and systems can be implemented in hardware, or a combination of hardware and software, and/or can be implemented from commercially available modules applications and devices. Where the implementation of the systems and methods described herein is at least partly based on use of microprocessors, the methods and systems can be implemented in one or more computer programs, where a computer program can be understood to include one or more processor executable instructions. The computer program(s) can execute on one or more programmable processors, and can be stored on one or more storage medium readable by the processor (including volatile and non-volatile memory and/or storage elements), one or more input devices, and/or one or more output devices. The processor thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation.

The computer program(s) can be implemented using one or more high level procedural or object-oriented programming languages to communicate with a computer system; however, the program(s) can be implemented in assembly or machine language, if desired. The language can be compiled or interpreted. The device(s) or computer systems that integrate with the processor(s) can include, for example, a personal computer(s), workstation (e.g., Sun, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a microprocessor" and "a processor", or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network using a variety of communications protocols, and unless otherwise specified, can be arranged to include a combination of external and internal memory devices, where such memory can be contiguous and/or partitioned based on the application. Accordingly, references to a database can be understood to include one or more memory associations, where such references can include commercially available database products (e.g., SQL, Informix, Oracle) and also proprietary databases, and may also include other structures for associating memory such as links, queues, graphs, trees, with such structures provided for illustration and not limitation.

A number of embodiments of the invention have been described. Nevertheless, it will be understood that various modifications may be made without departing from the spirit and scope of the invention. For example, as noted above, while the discussion above focused on the automatic registration of the coordinate system of a representation of the heart to the coordinate system of an object inserted into the medium enclosed within the heart (namely, the intracardiac blood), the procedures and systems described herein may also be adapted to be used for registering the coordinate system of representations of other objects that can be characterized as a distribution of materials having different conductivities.

Furthermore, while it is generally preferred that complete information about the position of the object is determined, such as the location of a point of the object and the orientation of the object with respect to that point; in other embodiments, the determined position for the object may include fewer than all of these degrees of freedom.

Accordingly, other embodiments are within the scope of the following claims.

What is claimed is:

1. A method for determining information about a location and orientation of a catheter in a patient's heart, the method comprising:

determining electrical signals as a function of relative position based on spatial information indicative of regions of different complex conductivity in the patient's heart cavity and conductivity values;

causing current to flow between each of three or more sets of current-injecting electrode source/sink pairs on a catheter inserted into the patient's heart;

measuring by multiple measuring electrodes located on the catheter, electrical signals in response to the current flow caused by each set of current injecting electrode source/sink pairs on the catheter;

determining the location and orientation of the catheter in the patient's heart based on the electrical signals measured by the multiple measuring electrodes located on the catheter in response to the current flow caused by the current injecting electrode source/sink pairs on the catheter and the determined electrical signals based on the spatial information;

measuring, by at least some of the multiple measuring electrodes on the catheter, electrical signals indicative of cardiac electrical activity; and determining information about electrical activity of the heart based on the measured electrical signals indicative of cardiac electrical activity and the determined location and orientation of the catheter in the patient's heart;

wherein causing the current to flow comprises injecting the current at frequencies spaced from those corresponding to the cardiac electrical activity and the determining the location and orientation of the catheter comprises frequency processing the measured electrical signal responsive to the injected current to distinguish electrical signals responsive to the injected current from those corresponding to the cardiac electrical activity.

2. The method of claim 1, further comprising:
displaying the information about the electrical activity of the heart on a representation of the patient's heart.

3. The method of claim 1, wherein determining the location and orientation of the catheter further comprises using an optimization algorithm that determines a conductivity value for each of one or more of the materials in the distribution of materials;
determines electrical signals based on the determined conductivity values and the spatial information about the distribution of materials as a function of the relative position; and minimizes differences between the measured electrical signals responsive to the injected current and the determined electrical signals.

4. The method of claim 1, wherein the spatial information about the distribution of materials is determined based on one or more of: a computed tomography (CT) image;
a magnetic resonance imaging (MRI) image; a fluoroscopic rotational angiography image; and an ultrasound image.

5. The method of claim 1, wherein determining the location and orientation of the catheter comprises frequency processing of the measured electrical signal responsive to the injected current to distinguish electrical signals responsive to the injected current from those corresponding to cardiac electrical activity.

6. The method of claim 1, further comprising:
receiving a signal indicative of the mechanical contraction of a patient's heart, the signal comprising an ECG signal; and
synchronizing the current to flow and the measuring with respect to a cardiac cycle by synchronizing the current to flow based on an R wave detected from the ECG signal.

7. A system for determining information about a location and orientation of a catheter in a patient's heart, the system comprising:
a catheter configured to be inserted into the patient's heart, the catheter including three or more sets of current-injecting electrodes and multiple measuring electrodes;
electronics coupled to the three or more sets of current-injecting electrodes for causing current to flow by injecting current in the patient's heart;
electronics coupled to the measuring electrodes for measuring an electrical signal in response to the current flow and for measuring electrical signals indicative of cardiac electrical activity; and
an electronic processor coupled to current causing and signal measuring electronics, wherein the electronic processor is configured to determine electrical signals as a function of relative position based on spatial information indicative of regions of different complex conductivity in the patient's heart cavity and conductivity values;
determine the location and orientation of the catheter in the patient's heart based on the electrical signals measured by the multiple spatially distributed measuring electrodes located on the catheter in response to the current flow by injecting currents at frequencies spaced from those corresponding to the cardiac electrical activity caused by the current injecting electrode source/sink pairs on the catheter; and
use electrical signals indicative of cardiac electrical activity measured by the electrodes on the catheter to determine information about electrical activity of the heart based on the measured electrical signals indicative of cardiac electrical activity and the determined location and orientation of the catheter in the patient's heart;
wherein the determining the location and orientation of the catheter comprises frequency processing the measured electrical signal responsive to the injected current to distinguish electrical signals responsive to the injected current from those corresponding to the cardiac electrical activity.

8. The system of claim 7, further comprising:
a display device configured to display the information about the electrical activity of the heart on a representation of the patient's heart.

9. The system of claim 7, wherein the determination of the location and orientation of the catheter by the electronic processor comprises determining the location and orientation of the catheter based on spatial information indicative of regions of different complex conductivity in the patient's heart cavity.

10. The system of claim 9, wherein the determination of the location and orientation of the catheter by the electronic processor comprises using an optimization algorithm that minimizes differences between the measured electrical signals responsive to the injected current and electrical signals determined from the spatial information about the distribution of materials as a function of the relative position.

11. The system of claim 9, wherein the electronic processor is further configured to determine the spatial information about the distribution of materials based on one or more of: a computed tomography (CT) image; a magnetic resonance imaging (MRI) image; a fluoroscopic rotational angiography image; and an ultrasound image.

12. The system of claim 7, wherein the surface of one or more of the current injecting electrodes has a coating to reduce its electrical impedance with respect to blood in the heart cavity.

13. The system of claim 7, wherein the current injection electrodes are positioned at opposite ends of a deployed configuration for the catheter with respect to each of multiple axes.

* * * * *